(12) United States Patent
Zhou et al.

(10) Patent No.: US 9,328,204 B2
(45) Date of Patent: May 3, 2016

(54) BENZODITHIOPHENE BASED COPOLYMER CONTAINING THIOPHENE PYRROLEDIONE UNITS AND PREPARING METHOD AND APPLICATIONS THEREOF

(71) Applicants: OCEAN'S KING LIGHTING SCIENCE & TECHNOLOGY CO., LTD., Shenzhen (CN); SHENZHEN OCEAN'S KING LIGHTING ENGINEERING CO., LTD., Shenzhen (CN)

(72) Inventors: Mingjie Zhou, Shenzhen (CN); Rong Guan, Shenzhen (CN); Manyuan Li, Shenzhen (CN); Jiale Huang, Shenzhen (CN); Naiyuan Li, Shenzhen (CN)

(73) Assignees: OCEAN'S KING LIGHTING SCIENCE & TECHNOLOGY CO., LTD., Shenzhen (CN); SHENZHEN OCEAN'S KING LIGHTING ENGINEERING CO., LTD., Shenzhen (CN)

( * ) Notice: Subject to any disclaimer, the term of this patent is extended or adjusted under 35 U.S.C. 154(b) by 0 days.

(21) Appl. No.: 14/647,652

(22) PCT Filed: Nov. 30, 2012

(86) PCT No.: PCT/CN2012/085685
§ 371 (c)(1),
(2) Date: May 27, 2015

(87) PCT Pub. No.: WO2014/082310
PCT Pub. Date: Jun. 5, 2014

(65) Prior Publication Data
US 2015/0307663 A1 Oct. 29, 2015

(51) Int. Cl.
*C08G 75/00* (2006.01)
*C08G 75/10* (2006.01)
(Continued)

(52) U.S. Cl.
CPC ............. *C08G 75/10* (2013.01); *B82Y 10/00* (2013.01); *C07D 495/04* (2013.01); *C08G 61/12* (2013.01);
(Continued)

(58) Field of Classification Search
CPC .......... C08G 61/12; C08G 2261/1412; C08G 2261/1424; C08G 2261/1428; C08G 2261/149; C08G 2261/3223; H05B 33/14; C09K 11/06; C07D 495/04; C07D 519/00
USPC ................................... 528/377, 380
See application file for complete search history.

(56) References Cited

U.S. PATENT DOCUMENTS

2011/0240973 A1  10/2011  Dueggeli et al.

FOREIGN PATENT DOCUMENTS

CN  102344550 A  2/2012

OTHER PUBLICATIONS

International Search Report dated Aug. 29, 2013.
(Continued)

*Primary Examiner* — Shane Fang
(74) *Attorney, Agent, or Firm* — Novak Druce Connolly Bove + Quigg LLP

(57) ABSTRACT

A benzodithiophene based copolymer containing thiophene pyrroledione units, a preparing method thereof, and applications of the copolymer in polymer solar cells, organic light-emitting, organic field effect transistors, organic optical storage, organic nonlinear materials or organic laser.

10 Claims, 3 Drawing Sheets

(51) Int. Cl.
| | |
|---|---|
| *C07D 495/04* | (2006.01) |
| *C09K 11/06* | (2006.01) |
| *H01L 51/00* | (2006.01) |
| *C08G 61/12* | (2006.01) |
| *B82Y 10/00* | (2011.01) |
| *H05B 33/14* | (2006.01) |
| *H01L 51/05* | (2006.01) |
| *H01L 51/50* | (2006.01) |
| *H01S 5/36* | (2006.01) |
| *H01L 51/42* | (2006.01) |
| *H01S 5/04* | (2006.01) |
| *C07D 519/00* | (2006.01) |

(52) U.S. Cl.
CPC ............. *C08G 61/126* (2013.01); *C09K 11/06* (2013.01); *H01L 51/0036* (2013.01); *H01L 51/0043* (2013.01); *H05B 33/14* (2013.01); *C07D 519/00* (2013.01); *C08G 2261/124* (2013.01); *C08G 2261/1412* (2013.01); *C08G 2261/3223* (2013.01); *C08G 2261/344* (2013.01); *C08G 2261/364* (2013.01); *C08G 2261/414* (2013.01); *C08G 2261/526* (2013.01); *C08G 2261/90* (2013.01); *C08G 2261/91* (2013.01); *C08G 2261/92* (2013.01); *C08G 2261/95* (2013.01); *C09K 2211/1483* (2013.01); *H01L 51/0047* (2013.01); *H01L 51/0558* (2013.01); *H01L 51/4253* (2013.01); *H01L 51/5012* (2013.01); *H01S 5/041* (2013.01); *H01S 5/36* (2013.01); *Y02E 10/549* (2013.01)

(56) References Cited

OTHER PUBLICATIONS

Li, Yongfang; High Efficiency Conjuated Polymer Donor and Fullerene Derivative Acceptor Photovoltaic Materials for Polymer Solar Cells, Polymer Bulletin, 2011,No. 10, pp. 33-49.

BENZODITHIOPHENE BASED COPOLYMER CONTAINING THIOPHENE PYRROLEDIONE UNITS AND PREPARING METHOD AND APPLICATIONS THEREOF

CROSS-REFERENCE TO RELATED APPLICATIONS

This application is a National Phase filing under 35 U.S.C. §371 of PCT/CN2012/085685 filed on Nov. 30, 2012, the entire contents of which is hereby incorporated by reference,

FIELD OF THE INVENTION

The present disclosure relates to the field of benzodithiophene based copolymer, more particularly relates to a benzodithiophene based copolymer containing thiophene pyrroledione units and preparing method and applications thereof.

BACKGROUND OF THE INVENTION

The organic solar cell, as a potential renewable energy, has attracted wide attention, which has some incomparable advantages better than inorganic solar cell, such as low cost, simple manufacturing process, light-weight, and it can be made flexibly in great area and so on. Over the past decade, the performance of the organic solar cell has improved, and the energy conversion efficiency is close to 10%.

The energy conversion efficiency of the organic solar cell has improved greatly; however, so far, the energy conversion efficiency of the organic solar cell is much lower than that of the inorganic solar cell. Therefore, in order to make the organic solar cell be implemented commercially, it is significant to develop a new organic semiconductor material for improving the efficiency of the organic solar cell.

In recent years, due to the development of the conjugated polymers in the design and the fabrication process of the device, the efficiency of the polymer solar cell has remarkably improved. In future, one challenge of the polymer solar cell is to synthesize a new P-type-conjugated polymer, which needs to have features of: (a) good solubility, which facilitates for processing and performing industrial production; (b) broad and strong absorption to the entire solar spectrum; (c) high carrier mobility, which facilitates for carrier transport. The researches have focused on broadening the light absorption range of the polymer materials and making the light absorption maximally cover the entire spectrum of solar light. Choosing an appropriate monomer in the semiconductor polymer backbone can broaden the light absorption range to infrared and near infrared. However, it fails to find such appropriate monomer in the prior art.

SUMMARY OF THE INVENTION

The present disclosure is directed to provide a benzodithiophene based copolymer containing thiophene pyrroledione units, which is copolymerized by benzodithiophene monomers and thiophene pyrroledione monomers, the absorption band-edge shifts towards the infrared and near infrared region for better matching the emission spectrum of the sunlight.

The present disclosure is also directed to provide a method for preparing a benzodithiophene based copolymer containing thiophene pyrroledione units.

The present disclosure is also directed to use of benzodithiophene based copolymer containing thiophene pyrroledione units in polymer solar cells, organic electroluminescent devices, organic field effect transistors, organic optical storage, organic non-linear devices, or organic laser.

A benzodithiophene based copolymer containing thiophene pyrroledione units has a structural formula:

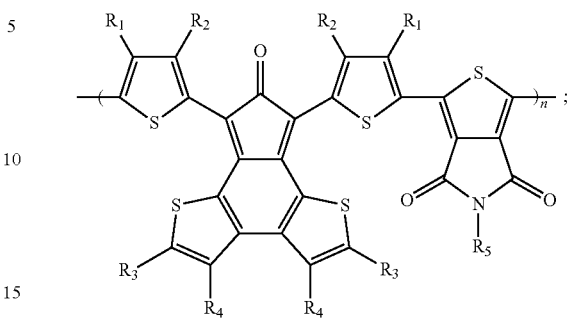

wherein $R_1$ and $R_2$ are selected from the group consisting of H, and $C_1$ to $C_{16}$ alkyl, respectively; $R_3$ and $R_4$ are selected from the group consisting of H, $C_1$ to $C_{16}$ alkyl, $C_1$ to $C_{16}$ alkoxy, and thienyl substituted by $C_1$ to $C_{16}$ alkyl, respectively; $R_5$ is $C_1$ to $C_{16}$ alkyl; n is a natural number from 8 to 82.

In the benzodithiophene based copolymer, the alkyl is a linear alkyl or branched alkyl; the alkoxy is a linear alkoxy or branched alkoxy.

In the benzodithiophene based copolymer, n is a natural number from 9 to 60.

In the benzodithiophene based copolymer, $R_1$ is the same as $R_2$, and/or $R_3$ is the same as $R_4$.

In the benzodithiophene based copolymer, $R_1$, $R_2$, $R_3$, $R_4$ and $R_5$ are selected from a combination of: $R_1$ and $R_2$ are H, $R_3$ and $R_4$ are methyl, $R_5$ is n-butyl; or $R_1$, $R_2$, $R_3$, and $R_4$ are H, $R_5$ is methyl; or $R_1$ is ethyl, $R_2$ is pentyl, $R_3$ is H, $R_4$ is 3-methyl thienyl, $R_5$ is 2-methyl butyl; or $R_1$ and $R_2$ are identical propyl, $R_3$ is 12 alkyl, $R_4$ is ethoxyl, $R_5$ is 2,4-dimethyl-3-ethyl heptyl; or $R_1$ is butyl, $R_2$ is 12 alkyl, $R_3$ is 14 alkoxy, $R_4$ is octyl, $R_5$ is 2,2,4-trimethyl pentyl; or $R_1$ and $R_2$ are identical H, $R_3$ is octoxy, $R_4$ is H, $R_5$ is 16 alkyl; or $R_1$ is hexyl, $R_2$ is H, $R_3$ is 2-methyl thienyl, $R_4$ is H, $R_5$ is octyl; or $R_1$ is 16 alkyl, $R_2$ is H, $R_3$ is methoxyl, $R_4$ is H, $R_5$ is methyl; or $R_1$ is H, $R_2$ is methyl, $R_3$ is 16 alkoxy, $R_4$ is H, $R_5$ is butyl; or $R_1$ and $R_2$ are identical methyl, $R_3$ is 16 alkoxy, $R_4$ is H, $R_5$ is butyl; or $R_1$ and $R_2$ are identical H, $R_3$ is hexyl, $R_4$ is H, $R_5$ is butyl; or $R_1$ and $R_2$ are identical H, $R_3$ is methyl, $R_4$ is H, $R_5$ is butyl; or $R_1$ and $R_2$ are identical H, $R_3$ and $R_4$ are identical H, $R_5$ is butyl.

A method for preparing a benzodithiophene based copolymer containing thiophene pyrroledione units includes the steps of:

adding M1 and M2 to a solvent in an oxygen-free environment;

M1

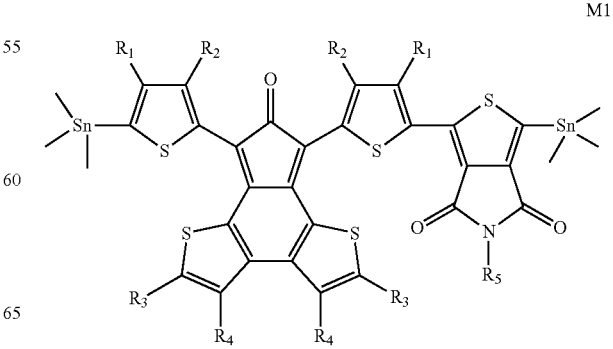

-continued

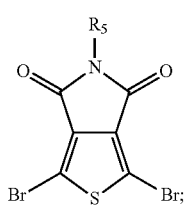

performing a refluxing reaction in the presence of catalyst; the reaction formula is as follows:

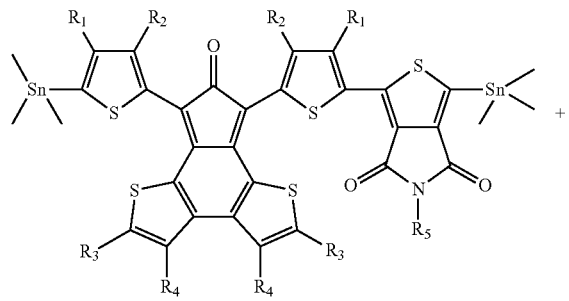

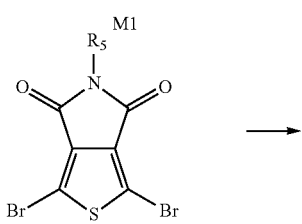

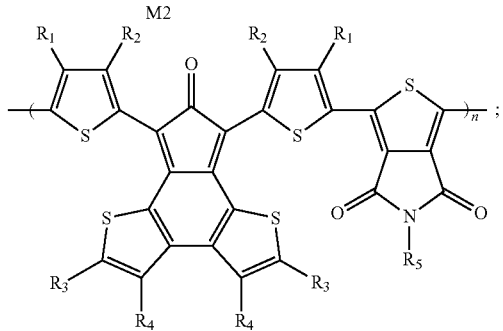

wherein $R_1$ and $R_2$ are selected from the group consisting of H, and $C_1$ to $C_{16}$ alkyl, respectively; $R_3$ and $R_4$ are selected from the group consisting of H, $C_1$ to $C_{16}$ alkyl, $C_1$ to $C_{16}$ alkoxy, and thienyl substituted by $C_1$ to $C_{16}$ alkyl, respectively; $R_5$ is $C_1$ to $C_{16}$ alkyl; n is a natural number from 7 to 80; wherein a molar ratio between M1 and M2 is 1:1 to 1.5:1; the solvent is at least one selected from the group consisting of toluene, tetrahydrofuran, benzene, and N,N-dimethylformamide; the catalyst is organic palladium or a mixture of organic palladium and organic phosphine ligand, a molar amount of the catalyst is 0.01% to 5% of the molar amount of the M2; the organic palladium is $Pd_2(dba)_3$, $Pd(PPh_3)_4$ or $Pd(PPh_3)_2Cl_2$, a molar ratio between the organic palladium and the organic phosphine ligand in the mixture is 1:2 to 1:20; the organic phosphine ligand is $P(o\text{-}Tol)_3$ or tricyclohexylphosphine; the reaction is performed at a temperature ranging from 60° C. to 120° C. for 12 to 72 hours.

In the method, M1 is synthesized by the steps of:

S1, dissolving a compound A with a proper amount of dichloromethane to form a solution, under a nitrogen atmosphere, adding the solution dropwise to anhydrous dichloromethane containing 1,3-dicyclohexylcarbodiimide and 4-dimethylaminopyridine by a syringe; wherein a molar ratio of the compound A, the 1,3-dicyclohexylcarbodiimide, and the 4-dimethylaminopyridine is 3:3:1, the reaction is performed for 8 to 24 hours to obtain a compound B, the reaction formula is as follows:

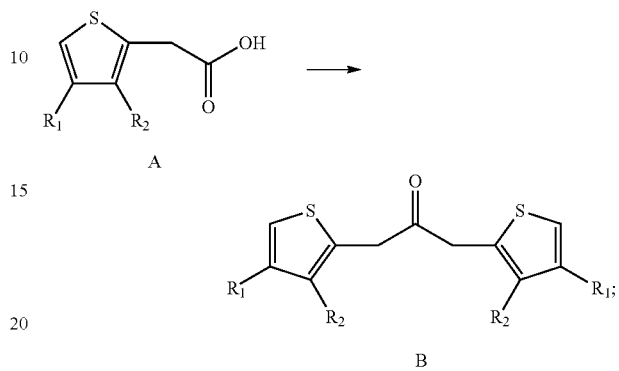

S2, adding the compound B and the compound C to a solvent according a molar ratio of 1:1, the solvent is ethanol or propanol; heating to 78° C. to 100° C. to perform a refluxing reaction, then adding a reducing agent, and reacting for additional 10 minutes to obtain a compound D; the reducing agent is potassium hydroxide or sodium hydroxide, a molar ratio between the reducing agent and the compound B is 5:1; the reaction is performed for additional 10 minutes after the reaction solution becomes dark green to obtain the compound D;

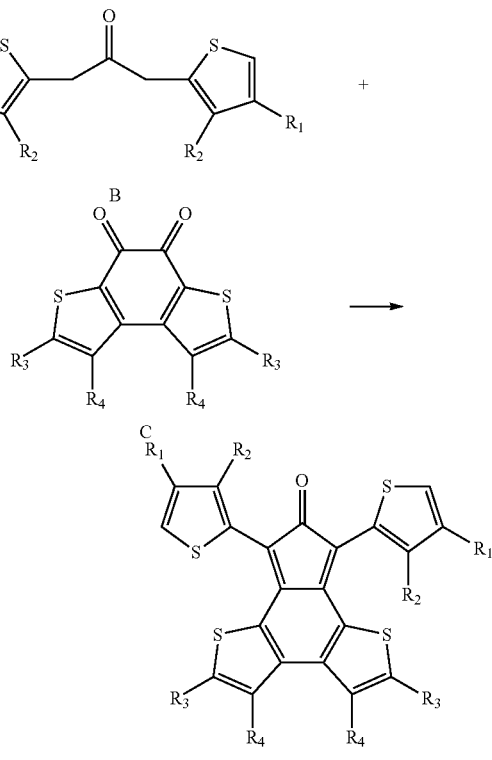

S3, under a nitrogen atmosphere, dissolving the compound D to anhydrous tetrahydrofuran and cooling to −78° C.; adding an n-hexane solution containing n-butyllithium slowly, a molar ratio between the n-butyllithium (n-BuLi) and the compound D is 1:2.5; reacting under stirring at a temperature of −78° C. for 2 hours; then adding trimethyl tin chloride, a molar ratio between the trimethyl tin chloride (Me₃SnLi) and the compound D is 2.5:1; incubating for 0.5 hours and then returning to room temperature; and reacting for additional 24 hours to obtain the compound M1; the reaction formula is as follows:

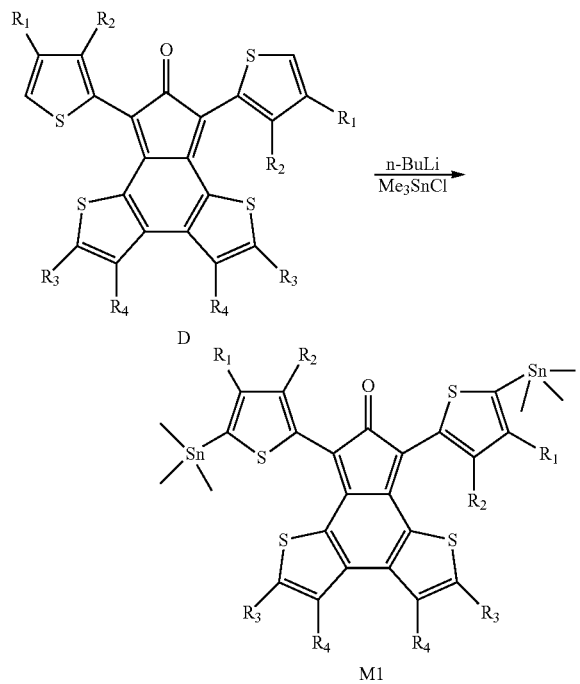

In the method, the alkyl is a linear alkyl or branched alkyl; the alkoxy is a linear alkoxy or branched alkoxy, n is a natural number from 9 to 60.

In the method, $R_1$ is the same as $R_2$, and/or $R_3$ is the same as $R_4$; or $R_1$, $R_2$, $R_3$, $R_4$ and $R_5$ are selected from a combination of: $R_1$ and $R_2$ are H, $R_3$ and $R_4$ are methyl, $R_5$ is n-butyl; or $R_1$, $R_2$, $R_3$, and $R_4$ are methyl; or $R_1$ is ethyl, $R_2$ is pentyl, $R_3$ is H, $R_4$ is 3-methyl thienyl, $R_5$ is 2-methyl butyl; or $R_1$ and $R_2$ are identical propyl, $R_3$ is 12 alkyl, $R_4$ is ethoxyl, $R_5$ is 2,4-dimethyl-3-ethyl heptyl; or $R_1$ is butyl, $R_2$ is 12 alkyl, $R_3$ is 14 alkoxy, $R_4$ is octyl, $R_5$ is 2,2,4-trimethyl pentyl; or $R_1$ and $R_2$ are identical H, $R_3$ is octoxy, $R_4$ is H, $R_5$ is 16 alkyl; or $R_1$ is hexyl, $R_2$ is H, $R_3$ is 2-methyl thienyl, $R_4$ is H, $R_5$ is octyl; or $R_1$ is 16 alkyl, $R_2$ is H, $R_3$ is methoxyl, $R_4$ is H, $R_5$ is methyl; or $R_1$ is H, $R_2$ is methyl, $R_3$ is 16 alkoxy, $R_4$ is H, $R_5$ is butyl; or $R_1$ and $R_2$ are identical methyl, $R_3$ is 16 alkoxy, $R_4$ is H, $R_5$ is butyl; or $R_1$ and $R_2$ are identical H, $R_3$ is hexyl, $R_4$ is H, $R_5$ is butyl; or $R_1$ and $R_2$ are identical H, $R_3$ is methyl, $R_4$ is H, $R_5$ is butyl; or $R_1$ and $R_2$ are identical H, $R_3$ and $R_4$ are identical H, $R_5$ is butyl.

One aspect of the present invention is to provide use of the benzodithiophene based copolymer containing thiophene pyrroledione units according to any one in polymer solar cells, polymer organic electroluminescent devices, polymer organic field effect transistors, polymer organic optical storage, polymer organic non-linear devices, or polymer organic laser and so on.

An appropriate monomer is selected for the semiconductor polymer backbone, which is beneficial to broaden the light absorption range to infrared and near infrared. In the benzodithiophene based copolymer containing thiophene pyrroledione units, an electron-rich donor and an electron-deficient acceptor unit are introduced to the polymer backbone; the energy gap of the conjugated polymer is reduced due to the "push-pull electrons" interaction of the donor and acceptor, thus the absorption band shifts towards low energy band of the infrared and near infrared. In the benzodithiophene derivatives, two thiophenes are connected in one plane by fused ring, its planarity and rigidity are enhanced, the copolymer has high optical, thermal and environmental stabilities. The central benzene ring decreases the electron-rich number of the thiophene rings located on two sides, thus the copolymer has much lower highest occupied orbital (HOMO) level. The π-π stockings between the π-bonds have much higher carrier mobility due to the existence of the extended conjugated π-bonds system. Therefore, the copolymer can be widely applied in the fields of organic electronics and so on; it can also be used to develop organic solar cell with low cost and high efficiency.

The main advantages of the present disclosure also include:

1. The synthetic routes of the benzodithiophene monomer M1 and thiophene pyrroledione monomer M2 are simple and mature, the introduction of the alkyl can improve the solubility and molecular weight of the product, thus the obtained polymer or oligomer can be spin-coated;

2. The benzodithiophene monomer M1 is a kind of excellent donor material and the thiophene pyrroledione monomer M2 is a kind of excellent receptor material, the polymer composed of the monomers M1 and M2 can form a donor-acceptor structure, on one hand, the stability of the material is improved, on the other hand, the band-gap of the material is reduced, thus the solar absorption range is broadened, and the photoelectric conversion efficiency is improved;

3. Stille coupling reaction is a very mature polymerization, it has high yield and mild conditions, and it is easy to control.

DETAILED DESCRIPTION OF THE EMBODIMENTS

Figure 1:
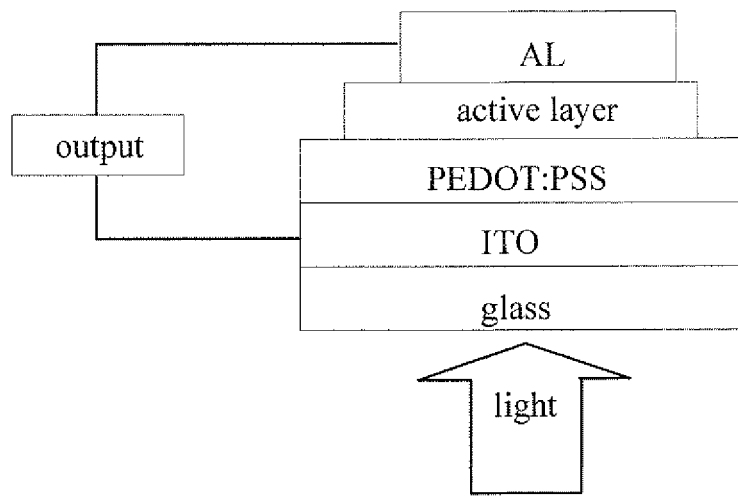
FIG. 1 is a schematic structure view of the organic solar cell according to example 9.

Some preferred embodiments of the present disclosure will be described in detail referring to the drawings.

A benzodithiophene based copolymer containing thiophene pyrroledione units is provided. First of all, one cyclopentadienyl ring of an inner ketone structure is fused on the benzene ring, which enhances the planarity and conjugation of the fused ring system. Therefore, the carrier mobility of the polymer is enhanced. Meanwhile, thiophene rings are introduced to both sides of the cyclopentadienone, and the alkyls are introduced to 3 and 4 sites of the thiophene to increase its solubility. The benzothiophene monomer is copolymerized with thiophene pyrroledione monomer of the strong receptor, and a "weak donor-strong acceptor" copolymer molecule is formed, which helps to reduce the optical energy gap, expand the light absorption range of the material, and improve sunlight utilization of the material.

In an embodiment, the benzodithiophene based copolymer containing thiophene pyrroledione units has a structural formula:

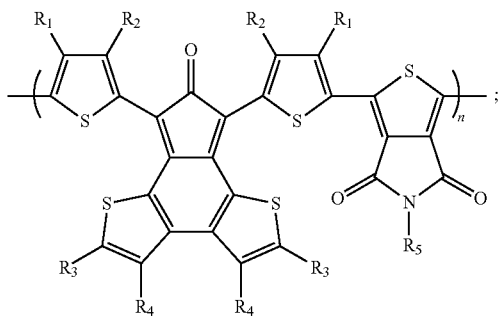

wherein $R_1$ and $R_2$ are identical or different, $R_1$ and $R_2$ are H or $C_1$ to $C_{16}$ alkyl, including linear alkyl or branched alkyl; or $R_1$ and $R_2$ are cycloalkyl and the like. $R_3$ and $R_4$ are identical or different, $R_3$ and $R_4$ are H, $C_1$ to $C_{16}$ alkyl, $C_1$ to $C_{16}$ alkoxy, or thienyl substituted by $C_1$ to $C_{16}$ alkyl; $R_5$ is $C_1$ to $C_{16}$ linear alkyl or branched alkyl, or $C_1$ to $C_{16}$ cycloalkyl and so on. In an embodiment, $R_5$ is 4-hydroxycyclohexyl, n is a natural number from 8 to 82. Alternatively, $R_1$, $R_2$, $R_3$, $R_4$ and $R_5$ are identical. For example, $R_1$, $R_2$, $R_3$, $R_4$ and $R_5$ are identical H, $CH_3$, or $C_1$ to $C_{16}$ alkyl, such as ethyl and the like.

In another embodiment, a method for preparing a benzodithiophene based copolymer containing thiophene pyrroledione units is provided, the reaction formula is as follows:

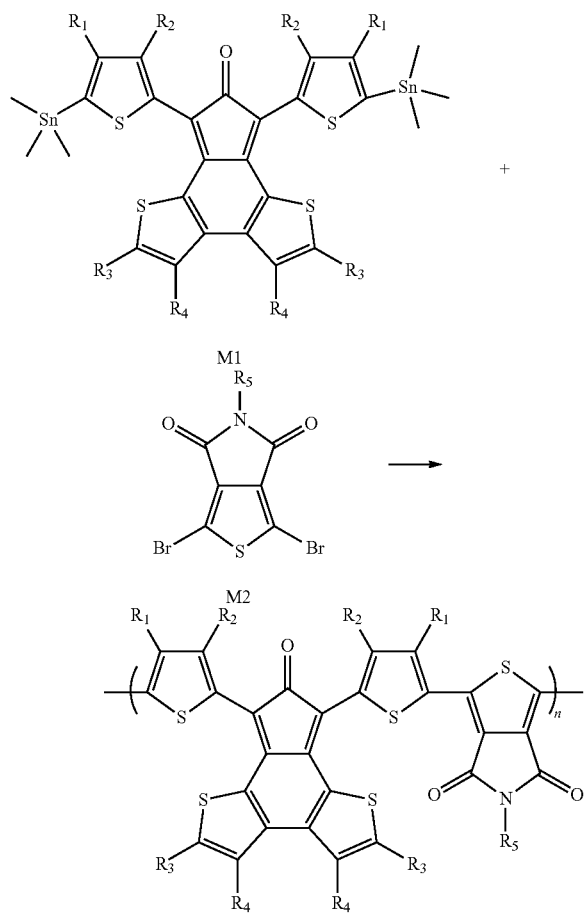

The method includes the steps of:
M1 and M2 are added to a solvent in an oxygen-free environment;

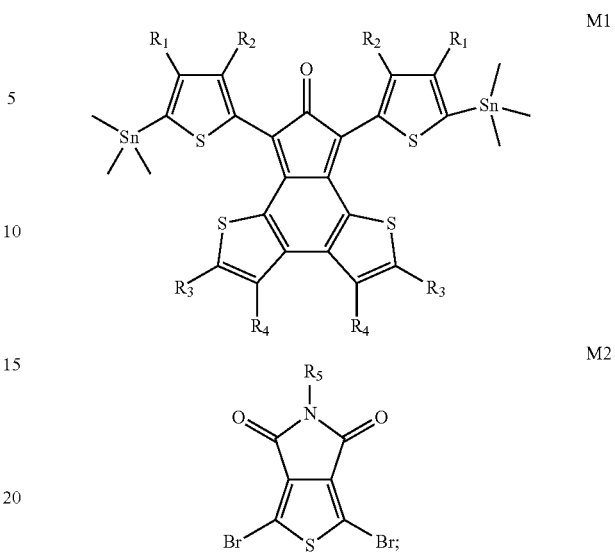

A refluxing reaction is performed in the presence of catalyst; and the benzodithiophene based copolymer containing thiophene pyrroledione units is obtained. A molar ratio between M1 and M2 is 1:1 to 1.5:1; in an embodiment, the molar ratio between M1 and M2 is 1.12:1, 1.2:1, 1.3:1, 1.35:1, 1.4:1 or 1.48:1 and so on.

In an embodiment, M2 is 1,3-dibromo-5-butyl-4H-thiophene [3,4-c] pyrrole -4, 5-dione or 1, 3-dibromo-5-(2-ethyl octane)-4H-thiophene [3, 4-c] pyrrole-4, 5-dione and the like, which is depended on the $R_5$, the preparation is referred to the method in the reference of *J. Mater. Chem.*, 2012, 22, 14639-14644.

Preferably, M1 and M2 are added to the solvent in an oxygen-free environment, and the refluxing reaction is performed in the presence of the catalyst. In an embodiment, the reaction is performed under a nitrogen atmosphere or under an inert gas atmosphere, such as nitrogen.

$R_1$ and $R_2$ are selected from H or $C_1$ to $C_{16}$ alkyl, respectively. In an embodiment, $R_1$ and $R_2$ are selected from H or $C_1$ to $C_{16}$ linear alkyl or branched alkyl, respectively, such as hydrogen, methyl, ethyl, propyl, n-pentyl, 2-methyl butyl, isobutyl, 4-methyl heptyl and the like. The repeating structural units of the benzodithiophene based copolymer are included in the parenthesis, the symbol of * represents a constitutional repeating unit connecting to the next unit.

$R_3$ and $R_4$ are selected from H, $C_1$ to $C_{16}$ alkyl, $C_1$ to $C_{16}$ alkoxy, or thienyl substituted by $C_1$ to $C_{16}$ alkyl, respectively. In an embodiment, $R_3$ and $R_4$ are selected from H, $C_1$ to $C_{16}$ linear alkyl or branched alkyl, $C_1$ to $C_{16}$ linear alkoxyl or branched alkoxyl, or thienyl substituted by $C_1$ to $C_{16}$ linear alkyl or thienyl substituted by $C_1$ to $C_{16}$ branched alkyl, respectively; such as hydrogen, n-pentyl, isobutyl, 4-methyl heptyl, 2-methyl 4-ethyl nonyl, iso-propoxy, n-pentyloxy, thienyl, 2-methyl thienyl, 3-ethyl thienyl, etc.

$R_5$ is $C_1$ to $C_{16}$ alkyl. In an embodiment, $R_5$ is $C_1$ to $C_{16}$ linear alkyl or branched alkyl or cycloalkyl, such as methyl, ethyl, n-pentyl, isobutyl, 4-methyl heptyl, 2-methyl 4-ethyl nonyl, and the like.

In an embodiment, $R_1$, $R_2$, $R_3$, $R_4$ and $R_5$ are identical H, $CH_3$, or $C_1$ to $C_{16}$ alkyl, such as ethyl and the like.

n is a natural number from 8 to 82. In an embodiment, n is 8, 9, 10, 11, 15 or 55, 60, 65, 72, 81, 82. Alternatively, n is a natural number from 9 to 60. Alternatively, n is a natural number from 10 to 50, or n is a natural number from 15 to 45. In an embodiment, n is 18, 20, 24, 25, 26, 27, 29, 31, 33, 35, 36, 38, 42 and the like. Generally, the ratio of reactants and/or reaction time are depended on the subsequent product application, accordingly, the degree of polymerization is adjusted.

The solvent is at least one selected from the group consisting of toluene, tetrahydrofuran, benzene, and N,N-dimethylformamide. The solvent is sufficient, which generally means that the solvent can completely dissolve the solute, or the solvent is enough for the reaction etc. In an embodiment, the solvent is toluene, tetrahydrofuran, benzene, and N,N-dimethylformamide; alternatively, the solvent is a mixed solvent of toluene and tetrahydrofuran with a molar ratio form 1:1 to 1.5:1; alternatively, the solvent is a mixed solvent of toluene, tetrahydrofuran and benzene with a molar ratio from 1:1:1 to 2:1:2 et al. Preferably, the solvent is a mixed solvent of toluene, tetrahydrofuran, benzene, and N,N-dimethylformamide with a molar ratio of 1:1:1:1 or a mixed solvent of toluene and benzene with a molar ratio of 1:1. Usually, the reaction is performed in oxygen-free environment; in an embodiment, the reaction is performed under nitrogen environment. Alternatively, the reaction is performed via filling with nitrogen or inert gas.

The catalyst is organic palladium or a mixture of organic palladium and organic phosphine ligand, the molar amount of the catalyst is 0.01%~5% of the molar amount of the M2. The organic palladium is $Pd_2(dba)_3$, $Pd(PPh_3)_4$ or $Pd(PPh_3)_2Cl_2$, a molar ratio between the organic palladium and the organic phosphine ligand in the mixture is 1:2 to 1:20. In an embodiment, the catalyst is organic palladium or a mixture of organic palladium and organic phosphine ligand, the molar amount of the catalyst is 0.01%~5% of the molar amount of the M2. The organic phosphine ligand is $P(o\text{-}Tol)_3$ or tricyclohexylphosphine or a combination thereof. In an embodiment, the molar amount of the catalyst is 0.1%, 0.12%, 0.2%, 0.3%, 0.45%, 0.67%, 0.8%, 1.1% or 2.3% of the molar amount of the M2. The organic palladium is $Pd_2(dba)_3$, $Pd(PPh_3)_4$ or $Pd(PPh_3)_2Cl_2$. A molar ratio between the organic palladium and organic phosphine ligand in the mixture is 1:2 to 1:20. In an embodiment, a molar ratio between the organic palladium and organic phosphine ligand in the mixture is 1:2.5, 1:3, 1:5, 1:6.8, 1:8, 1:9, 1:11, 1:14, 1:18 or 1:19.5. In an embodiment, a molar ratio between the $Pd_2(dba)_3$ and $P(o\text{-}Tol)_3$ is 1:3 or 1:2.

The reaction is performed at a temperature ranging from 60° C. to 120° C. for 12 to 72 hours. In an embodiment, the reaction temperature is 61° C., 65° C., 72° C., 78° C., 80.5° C., 87° C., 91° C., 105° C. or 119° C. The reaction time is 12.5 hours, 14 hours, 22 hours, 24 hours, 28 hours, 37 hours, 44 hours, 49 hours, 56 hours, 64 hours or 71 hours. Preferably, the reaction temperature and reaction time are mutual depended to each other, when the reaction temperature is high, then the reaction time is relatively reduced, which can be adjusted according to actual situation.

In an embodiment, M1 is synthesized by the steps of:

Step one, the compound A is dissolved with an appropriate amount of dichloromethane to form a solution, under a nitrogen atmosphere, the solution is added to anhydrous dichloromethane containing DCC (1,3-dicyclohexylcarbodiimide) and DMPA (4-dimethylaminopyridine) dropwise by a syringe, wherein a molar ratio of the compound A, DDC and DMAP is 3:3:1, the reaction is performed over night to obtain the product of the compound B, the reaction formula is as follows:

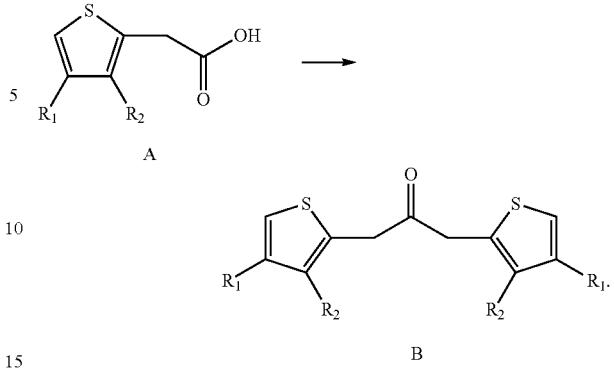

In an embodiment, the reaction is performed for 8 to 24 hours. In an embodiment, the molar ratio of A, DCC and DMAP is 3.5:3:1, 3:3:1.5, or 2:2.2:1. Alternatively, the reaction is performed for 8.5 hours, 9 hours, 11 hours, 15.5 hours, 18 hours or 22 hours, etc.

Step two: the compound B and the compound C are added to the solvent with a molar ratio of 1.0:1.0, then heated to 78° C. to 100° C. to perform a refluxing reaction, and an appropriate amount of potassium hydroxide/sodium hydroxide is added, wherein a molar ratio of the potassium hydroxide/sodium hydroxide and the compound B is 5:1. The reaction is performed for additional 8 to 12 minutes after the reaction solution becomes dark green, preferably for 10 minutes, the product is obtained, i.e. the compound D. The solvent is ethanol, propanol, etc. The reaction formula is as follows:

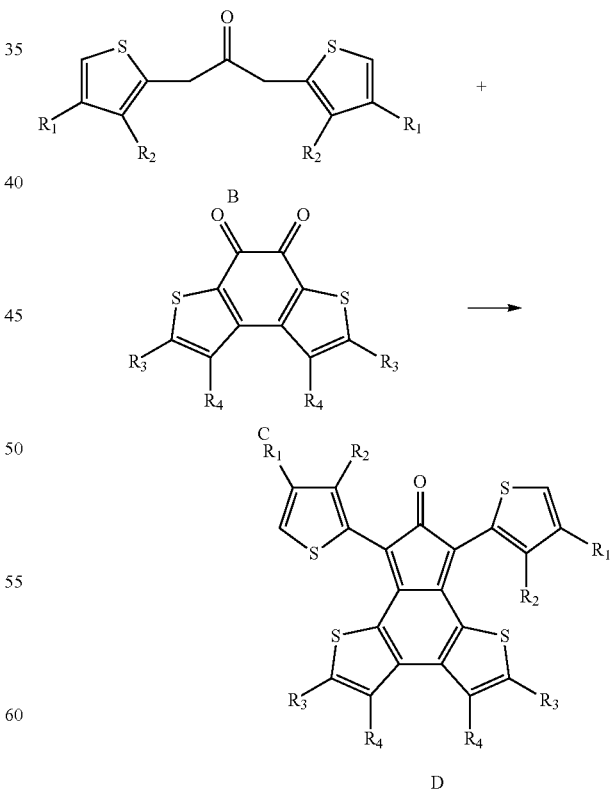

In an embodiment, a molar ratio of the compound B and the compound C is 1:1, the compound B and the compound C are added to ethanol, propanol or a mixture thereof. In an embodiment, a molar ratio of the ethanol and the propanol is 1:1, 2:1, 1:2 etc. The solution is heated to 78° C. to 100° C. for refluxing. In an embodiment, the solution is uniformly heated to 80° C., 85° C., 90° C., 91° C., 96° C. or 99° C. for refluxing reaction. A reducing agent is added prior to heating, during heating or when the temperature is more than 78° C. Preferably, the reducing agent is added when the temperature is more than 78° C. In an embodiment, the reducing agent is sodium hydroxide, the molar ratio of the sodium hydroxide and the compound B is 5:1.

Step three: under a nitrogen atmosphere, the anhydrous tetrahydrofuran solution of the compound D is cooled to −78° C., then n-BuLi(n-butyllithium) solution is slowly added, a molar ratio of the n-BuLi and the compound D is 1:2.5. The reaction is performed for 2 hours at −78° C. in stirring, then the trimethyl tin chloride reagent is added, a molar ratio of Me$_3$SnCl and D is 2.5:1, the reaction solution returns to room temperature after incubating for 0.5 hours, and then reaction is performed for additional 24 hours, the product is obtained, i.e. the compound M1; the reaction formula is as follows:

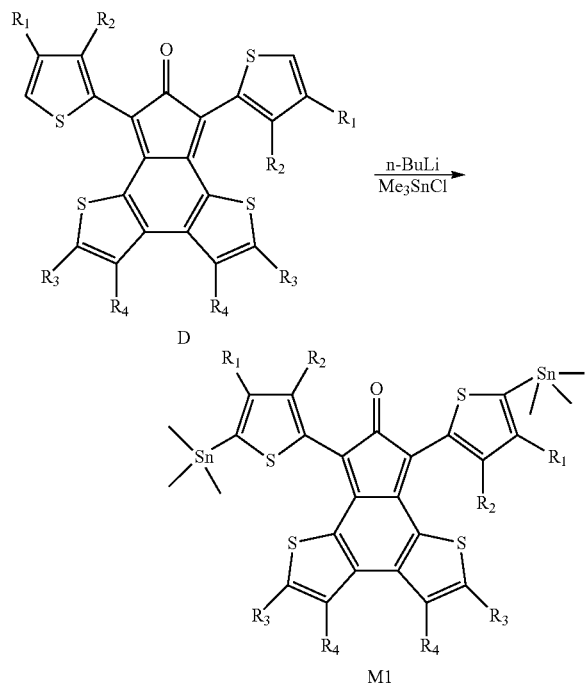

In an embodiment, $R_1$ and $R_2$ are identical, and $R_3$ and $R_4$ are identical. Alternatively, $R_1$ and $R_2$ are identical, $R_3$ and $R_4$ are different. Alternatively, $R_1$ and $R_2$ are different, $R_3$ and $R_4$ are identical. Alternatively, $R_1$, $R_2$, $R_3$, $R_4$, and $R_5$ are selected from a combination of: $R_1$ and $R_2$ are H, $R_3$ and $R_4$ are methyl, $R_5$ is n-butyl; alternatively, $R_1$, $R_2$, $R_3$, $R_4$ are H, $R_5$ is methyl; alternatively, $R_1$ is ethyl, $R_2$ is pentyl, $R_3$ is H, $R_4$ is 3-methyl thienyl, $R_5$ is 2-methyl butyl; alternatively, $R_1$ and $R_2$ are identical propyl, $R_3$ is 12 alkyl; $R_4$ is ethoxyl; $R_5$ is 2,4-dimethyl-3-ethyl heptyl; alternatively, $R_1$ is butyl, $R_2$ is 12 alkyl, $R_3$ is 14 alkoxy, $R_4$ is octyl, $R_5$ is 2,2,4-trimethyl pentyl; alternatively, $R_1$ and $R_2$ are identical H, $R_3$ is octoxy, $R_4$ is H, $R_5$ is 16 alkyl; alternatively, $R_1$ is hexyl, $R_2$ is H, $R_3$ is 2-methyl thienyl, $R_4$ is H, $R_5$ is octyl; alternatively, $R_1$ is 16 alkyl, $R_2$ is H; $R_3$ is methoxyl; $R_4$ is H, $R_5$ is methyl; alternatively, $R_1$ is H, $R_2$ is methyl, $R_3$ is 16 alkoxy, $R_4$ is H, $R_5$ is butyl; alternatively, $R_1$ and $R_2$ are identical methyl, $R_3$ is 16 alkoxy, $R_4$ is H, $R_5$ is butyl; alternatively, $R_1$ and $R_2$ are identical H, $R_3$ is hexyl; $R_4$ is H, $R_5$ is butyl; alternatively, $R_1$ and $R_2$ are identical H, $R_3$ is methyl, $R_4$ is H, $R_5$ is butyl; alternatively, $R_1$ and $R_2$ are identical H, $R_3$ and $R_4$ are identical H, $R_5$ is butyl.

In an embodiment, the benzodithiophene based copolymer containing thiophene pyrroledione units has a structural formula:

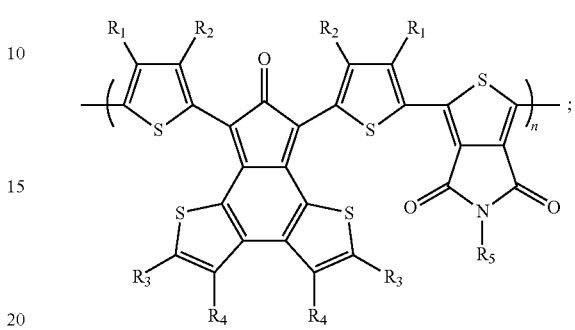

wherein $R_1$ and $R_2$ are identical or different, and $R_1$ and $R_2$ are selected from the group consisting of H, and $C_1$ to $C_{16}$ alkyl, respectively; $R_3$ and $R_4$ are identical or different, $R_3$ and $R_4$ are selected from the group consisting of H, $C_1$ to $C_{16}$ alkyl, $C_1$ to $C_{16}$ alkoxy, or thienyl substituted by $C_1$ to $C_{16}$ alkyl, respectively; $R_5$ is $C_1$ to $C_{16}$ linear alkyl or branched alkyl; n is a natural number from 8 to 60.

In an embodiment, $R_1$ and $R_2$ are selected from the group consisting of H and $C_1$ to $C_{16}$ alkyl, respectively. In an embodiment, $R_1$ and $R_2$ are selected from the group consisting of H and $C_1$ to $C_{16}$ linear or branched alkyl, respectively; such as hydrogen, methyl, ethyl, propyl, n-pentyl, 2-methylbutyl, isobutyl, 4-methyl heptyl, decyl, linear or branched 12 alkyl, linear or branched 16 alkyl and the like. The repeating structural units of the benzodithiophene based copolymer are included in the parenthesis, the symbol * represents a constitutional repeating unit connecting to the next unit.

$R_3$ and $R_4$ are selected from the group consisting of H, $C_1$ to $C_{16}$ alkyl, $C_1$ to $C_{16}$ alkoxy, and thienyl substituted by $C_1$ to $C_{16}$ alkyl, respectively. In an embodiment, $R_3$ and $R_4$ are selected from the group consisting of H, $C_1$ to $C_{16}$ linear alkyl or branched alkyl, $C_1$ to $C_{16}$ linear alkoxy or branched alkoxy, and thienyl substituted by $C_1$ to $C_{16}$ linear alkyl or branched alkyl, respectively; such as hydrogen, n-pentyl, isobutyl, 4-methyl heptyl, 2-methyl 4-ethyl nonyl, iso-propoxy, n-pentyloxy, thienyl, 2-methyl thienyl, 3-ethyl thienyl, etc.

$R_5$ is $C_1$ to $C_{16}$ alkyl. In an embodiment, $R_5$ is $C_1$ to $C_{16}$ linear or branched alkyl, such as methyl, ethyl, n-pentyl, isobutyl, 4-methyl heptyl, 2-methyl 4-ethyl nonyl, and the like.

In an embodiment, the alkyl in the aforementioned embodiments is partially or fully fluorinated.

In an embodiment, n is a natural number from 8 to 82. Generally, the ratio of reactants and/or the reaction time are depended on the applications of the subsequent products; accordingly, the degree of polymerization is adjusted.

In the aforementioned embodiments, $R_1$ and $R_2$ are identical, and $R_3$ and $R_4$ are identical. Alternatively, $R_1$ and $R_2$ are identical, $R_3$ and $R_4$ are different. Alternatively, $R_1$ and $R_2$ are different, $R_3$ and $R_4$ are identical.

In an embodiment, in the benzodithiophene based copolymer, $R_1$ and $R_2$ are H, $R_3$ and $R_4$ are methyl, $R_5$ is n-butyl. Alternatively, $R_1$, $R_2$, $R_3$, and $R_4$ are H, $R_5$ is methyl.

In an embodiment, $R_1$ is ethyl, $R_2$ is pentyl, $R_3$ is H, $R_4$ is 3-methyl thienyl, $R_5$ is 2-methyl butyl. Alternatively, $R_2$ is n-pentyl or isopentyl, i.e. both linear alkyl and branched alkyl are suitable, similarly hereinafter.

In an embodiment, $R_1$ and $R_2$ are indentical propyl, $R_3$ is 12 alkyl, $R_4$ is ethoxyl, $R_5$ is 2,4-dimethyl-3-ethyl heptyl.

In an embodiment, $R_1$ is butyl, $R_2$ is 12 alkyl, $R_3$ is 14 alkoxy, $R_4$ is octyl, $R_5$ is 2,2,4-trimethyl pentyl.

For a better understanding of the present disclosure, the technical solution of the present disclosure is further illustrated by the specific examples.

Example 1

A benzodithiophene based copolymer containing thiophene pyrroledione units having a following structural formula is provided.

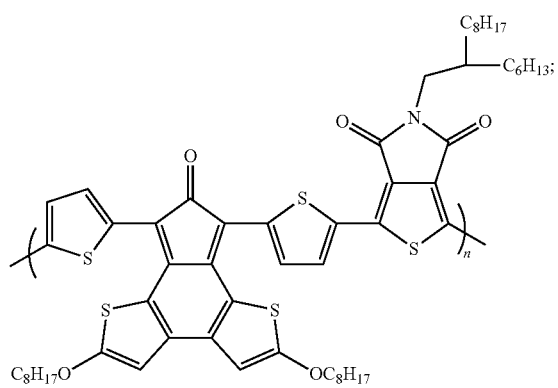

wherein $R_1$ and $R_2$ are identical H, $R_3$ is octoxy, $R_4$ is H, $R_5$ is 16 alkyl, such as 2-hexyl decyl shown in the formula, n=60.

The preparation of the benzodithiophene based copolymer containing thiophene pyrroledione units includes the steps of:

Step one, the preparation of 1,3-bis(2-thiophene) acetone was described below.

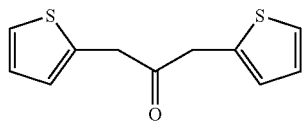 [SMILES: O=C(Cc1cccs1)Cc1cccs1]

First, 7.6 g (36.8 mmol) of DCC and 1.23 g (10 mmol) of DMAP were dissolved in 70 mL of dichloromethane via anhydrous treatment to form a reaction solution; under a nitrogen atmosphere, 70 mL of dichloromethane solution containing 5 g (35.2 mmol) of 2-thiophene acetic acid was added dropwise to the reaction solution, the reaction was performed overnight. After the reaction was finished, the reaction solution was filtered, recrystallized with n-hexane for twice, and purified by column chromatography to obtain a product.

MALDI-TOF-MS (Matrix-Assisted Laser Desorption/Ionization Time of Flight Mass Spectrometry) mass-to-charge ratio (m/z) was 222.3 (M$^+$).

For example, the dichloromethane was treated with calcium chloride or potassium carbonate to obtain anhydrous dichloromethane, then stirred and kept overnight, and distilled.

Step two, the preparation of 2, 7-dioctyloxybenzo [1,2-b:4,3-b'] dithiophene-4,5-diketone was described below:

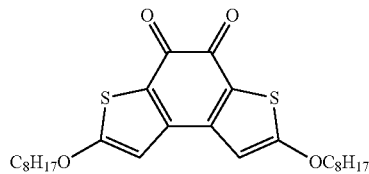

25.4 g (i.e. 60 mmol) of 4, 4'-bis(2-octyloxy)thiophene was added to 400 mL of dry 1,2-dichloroethane, i.e. 25.4 g (i.e. 60 mmol) of 4, 4'-bis(2-octyloxy)thiophene was added to a reaction flask having 400 mL of 1,2-dichloroethane or 400 mL of 1,2-dichloroethane via dry treatment, similarly hereinafter; then 3 mL (i.e. 34.5 mmol) of oxalyl chloride was added to the reaction flask for three times within 5 days, and the refluxing reaction was performed for 15 days under an argon atmosphere. After the reaction was finished, the reaction solution was cooled to room temperature; and frozen overnight in the refrigerator; then filtered to obtain a red solid, and the red solid was washed with n-hexane and ethanol successively to obtain a product.

MALDI-TOF-MS (m/z) was 477.0 (M$^+$)

In an embodiment, 1 mL of oxalyl chloride was added on the first day, 1 mL of oxalyl chloride was added on the third day, 1 mL of oxalyl chloride was added on the fifth day. Alternatively, 1 mL of oxalyl chloride was added on the first day, 0.5 mL of oxalyl chloride was added on the second day, 1.5 mL of oxalyl chloride was added on the fifth day. Alternatively, 0.5 mL of oxalyl chloride was added on the first day, 1 mL of oxalyl chloride was added on the third day, 1.5 mL of oxalyl chloride was added on the fifth day.

Step three, the preparation of 2,5-dioctyloxy-7,9-bis(2-thiophene)-8H-cyclopentadienebenzo [1,2-b:4,3-b'] dithiophene-8-ketone was described below:

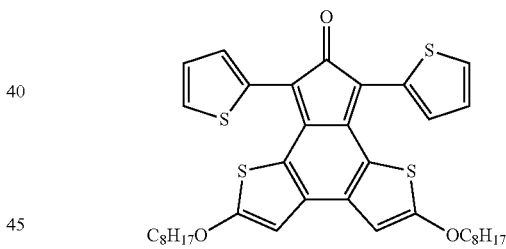

1.2 g (5.4 mmol) of 1,3-bis(2-thiophene) acetone, 2.7 g (5.4 mmol) of 2,7-dioctyloxy-4,5-diketone, and 40 mL of ethanol were successively added to 250 mL of a single flask, and then heated for refluxing. A small amount of potassium hydroxide was dissolved in 2 mL of ethanol; then added to the reaction flask dropwise via a syringe. When the reaction solution turned dark green, the reaction was performed for additional 10 minutes and then stopped; the reaction solution was poured into an ice-water bath. The reaction solution was filtrated, and washed with ethanol, hot n-hexane for several times, and dried to obtain a solid product. In an embodiment, the temperature of the n-hexane was the same as the reaction temperature, or the difference between the temperature of the n-hexane and the reaction temperature was 5° C. Alternatively, a molar ratio of the potassium hydroxide and the 1,3-bis(2-thiophene) acetone was 5:1.

MALDI-TOF-MS (m/z): 679.0 (M$^+$).

Step four, the preparation of 2, 5-dioctyloxy-7, 9-bis(2-trimethyltin-5-thiophen)-8H-cyclopentadiene benzo [1,2-b:4,3-b'] dithiophene-8-ketone was described below:

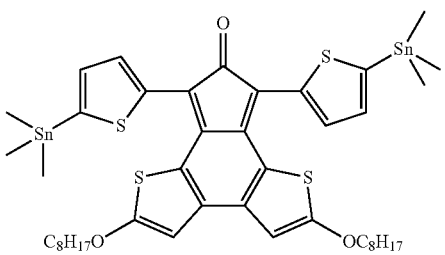

Under a nitrogen atmosphere, 6.79 g (10 mmol) of the 2,5-dioctyloxy-7,9-bis(2-thiophene)-8H-cyclopentadiene benzo [1,2-b:4,3-b'] dithiophene-8-ketone and 120 mL of anhydrous THF were cooled to −78° C.; then 5 mL (12 mmol) of n-butyllithium in 2.5 M hexane solution was slowly added, after that, the reaction solution was incubated at −78° C. for 2 hours; then 4.5 mL (15 mmol) of trimethyl tin chloride was added, the reaction solution naturally returned to room temperature after incubating for 0.5 hours, then the reaction was performed for additional 24 hours and stopped. 50 mL of hexane was added for dilution, then the reaction solution was slowly poured into ice water, an organic phase product was obtained by extraction, the organic phase product was washed with 5% $NaHCO_3$ and saturated NaCl solution, respectively, then dried with anhydrous magnesium sulfate, filtrated, evaporated, and distilled under reduced pressure, excess trimethyl tin chloride was distilled out and a product was obtained.

MALDI-TOF-MS (m/z): 1004.6 ($M^+$).

Step five, the preparation of benzodithiophene based copolymer containing thiophene pyrroledione units was described below:

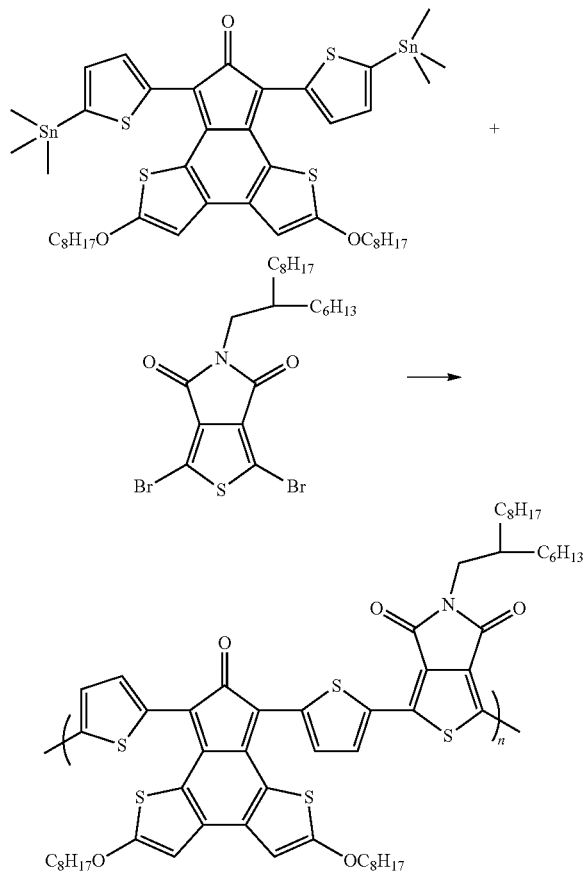

Under a nitrogen atmosphere, 0.5 g (0.5 mmol) of 2, 5-dioctyloxy-7, 9-bis (2-trimethyltin-5-thiophen)-8H-cyclopentadiene benzo [1,2-b:4,3-b'] dithiophene-8-ketone and 0.27 g (0.5 mmol) of 1, 3-dibromo-5-(2-ethyl decyl)-4H-thiophene [3, 4-c] pyrrole-4, 5-dione (corresponding to the structural formula in the above equation, hereinafter similarly) were added to a reaction flask containing 10 mL of dry toluene, the reaction mixture was stirred under a stream of nitrogen for 15 minutes, and a catalyst of $Pd_2(dba)_3$ and $P(o-Tol)_3$ was added rapidly to the reaction flask; wherein $Pd_2(dba)_3$ was 23 mg (0.025 mmol, 5% mol); $P(o-Tol)_3$ was 152 mg (0.5 mmol); a molar ratio of $Pd_2(dba)_3$ and $P(o-Tol)_3$ was 1:20.

After the reaction mixture was stirred under a stream of nitrogen for 15 minutes, the reaction mixture was heated to 80° C. for refluxing, and the reaction solution was stirred for 72 hours then the reaction was stopped, after the reaction solution was cooled to room temperature, the reaction solution was dried to about 5 mL via reduced pressure distillation, then dropped into 300 mL of dry methanol, and continuously stirred for about 4 hours, a solid was gradually precipitated, a solid powder was obtained via suction filtration and dry. The solid powder was dissolved with chloroform, purified by neutral alumina column chromatography to remove the catalyst of $Pd_2(dba)_3$, the polymer solution was evaporated to about 5 mL, and the 5 mL solution was dropped into a methanol solvent and stirred for several hours, finally a polymer was collected and dried, the polymer was extracted with Soxhlet extractor, thus the monodispersity of the polymer molecular weight was improved.

The molecular weight was tested via Gel Permeation Chromatography (GPC). GPC: Mn=67320, Polydispersity coefficient index (PDI)=1.5.

Example 2

A benzodithiophene based copolymer containing thiophene pyrroledione units having a following structural formula is provided.

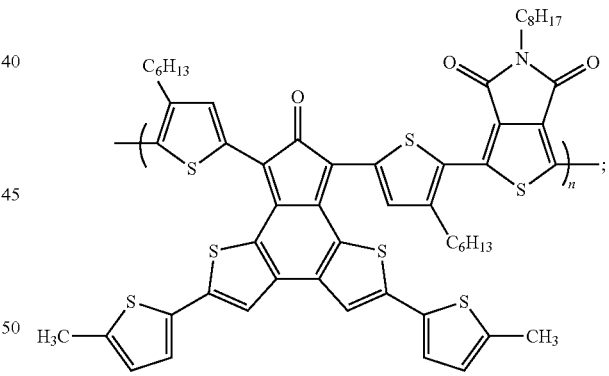

wherein $R_1$ is hexyl, $R_2$ is H, $R_3$ is 2-methyl thienyl; $R_4$ is H, $R_5$ is octyl, such as 1-n-octyl, n=55.

The preparation of the benzodithiophene based copolymer containing thiophene pyrroledione units includes the steps of:

Step one, the preparation of bis (4-dihexyl-2-thiophene) acetone was described below.

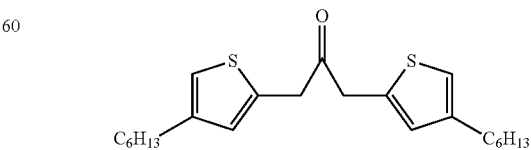

First, 7.6 g of DCC and 1.23 g of DMAP were dissolved in 70 mL of dichloromethane via anhydrous treatment to form a reaction solution; under a nitrogen atmosphere, 60 mL of dichloromethane solution containing 7.6 g of 4-hexyl-2-thiophene acetic acid was added to the reaction solution, the reaction was performed overnight. After the reaction was finished, the reaction solution was filtered, recrystallized with n-hexane for twice, and purified by column chromatography to obtain a product.

MALDI-TOF-MS (m/z): 391 (M$^+$)

Step two, the preparation of 2, 7-bis(2-methyl-5-thiophen) benzo [1,2-b:4,3-b'] dithiophene-4,5-diketone was described below:

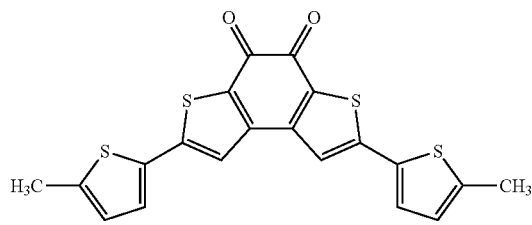

21.5 g (60 mmol) of 4, 4'-bis(2-methyl-5-thiophen) thiophene was added to 350 mL of dry 1,2-dichloroethane, then 3 mL (34.5 mmol) of oxalyl chloride was added to the reaction flask for three times within 5 days, and the refluxing reaction was performed under an argon atmosphere for 15 days. After the reaction was finished, the reaction solution was cooled to room temperature; and frozen overnight in the refrigerator; then filtered to obtain a red solid; then the red solid was washed with n-hexane and ethanol successively to obtain a product.

MALDI-TOF-MS (m/z): 413.0 (M$^+$).

Step three, the preparation of 2,5-bis(2-methyl-5-thiophen)-7,9-bis(4-hexyl-2-thiophene)-8H-cyclopentadiene benzo [1,2-b:4,3-b'] dithiophene-8-ketone was described below

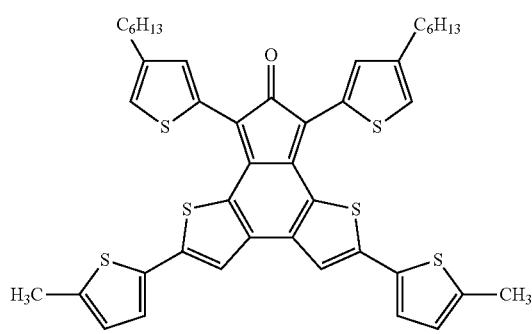

2.1 g (5.4 mmol) of bis(4-hexyl-2-thiophene) acetone, 2.2 g (5.4 mmol) of 2, 7-bis(2-methyl-5-thiophen) benzo [1,2-b:4,3-b] dithiophene-4,5-diketone, and 60 mL of ethanol were successively added to 250 mL of single flask, and then heated for refluxing. A small amount of potassium hydroxide was dissolved in 2 mL of ethanol; then added to the reaction flask dropwise via a syringe. When the reaction solution turned dark green, the reaction was performed for additional 10 minutes and then stopped; the reaction solution was poured into an ice-water bath, then the reaction solution was filtrated, and washed with ethanol, hot n-hexane for several times, and dried to obtain a solid product.

MALDI-TOF-MS (m/z): 765.0 (M$^+$).

Step four, the preparation of 2,5-bis (2-methyl-5-thiophen)-7,9-bis(4-hexyl-2-trimethyltin-5-thiophen)-8H-cyclopentadiene benzo [1,2-b:4,3-b'] dithiophene-8-ketone was described below:

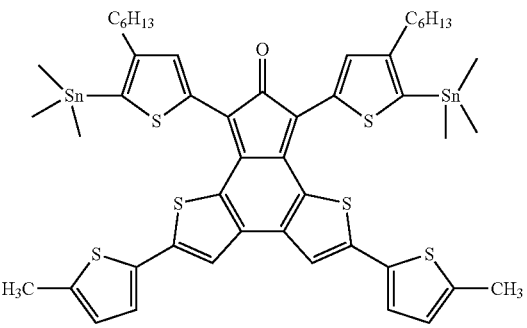

Under a nitrogen atmosphere, 7.65 g (10 mmol) of the 2,5-bis(2-methyl-5-thiophen)-7,9-bis (4-hexyl-2-thiophene)-8H-cyclopentadiene benzo [1,2-b:4,3-b'] dithiophene-8-ketone and 150 mL of anhydrous THF were cooled to −78° C. 5 mL (12 mmol) of n-butyllithium of hexane solution (2.5 M) was slowly added, after that, the reaction solution was incubated at −78° C. for 2 hours; then 4.5 mL (15 mmol) of trimethyl tin chloride was added, the reaction solution was naturally recovered to room temperature after incubating for 0.5 hours, the reaction was performed for additional 24 hours and then stopped. 50 mL of hexane was added for dilution, then the reaction solution was slowly poured into ice water, an organic phase product was obtained by extraction, the organic phase product was washed with 5% NaHCO$_3$ and saturated NaCl solution, respectively, then dried with anhydrous magnesium sulfate, filtrated, evaporated, and distilled under reduced pressure, excess trimethyl tin chloride was distilled out and a product was obtained.

MALDI-TOF-MS (m/z): 1093 (M$^+$).

Step five, the preparation of benzodithiophene based copolymer containing thiophene pyrroledione units was described below:

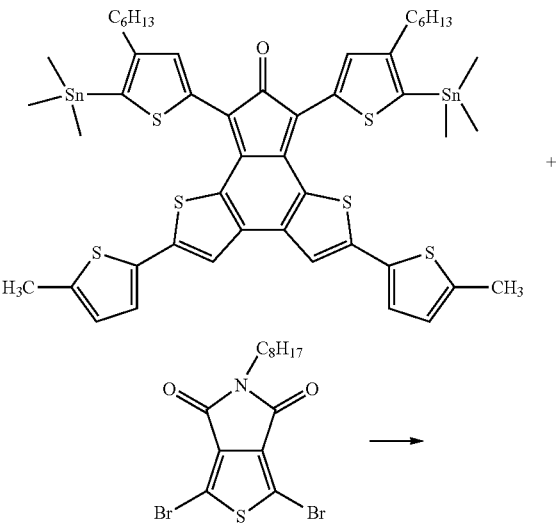

-continued

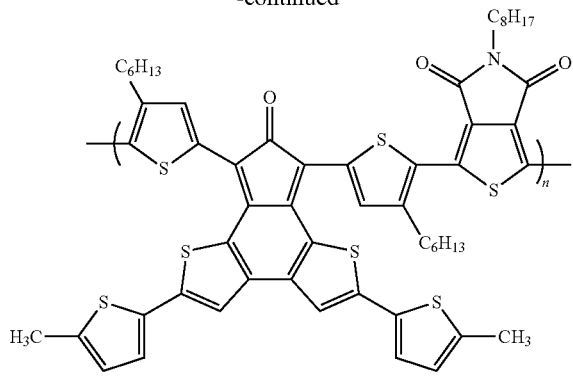

Under a nitrogen atmosphere, 0.82 g (0.75 mmol) of 2,5-bis(2-methyl-5-thiophen)-7,9-bis(4-hexyl-2-trimethyltin-5-thiophen)-8H-cyclopentadiene benzo [1,2-b:4,3-b'] dithiophene-8-ketone and 0.21 g (0.5 mmol) of 1, 3-dibromo-5-octyl-4H-thiophene[3, 4-c] pyrrole-4, 5-dione were added to a reaction flask containing 10 mL of dry tetrahydrofuran, i.e. a reaction flask containing 10 mL of dry tetrahydrofuran or a reaction flask containing 10 mL of tetrahydrofuran via dry treatment, the reaction mixture was stirred under a stream of nitrogen for 15 minutes, and a catalyst of 14 mg (0.015 mmol, 3% mol) of $Pd_2(dba)_3$ and 68 mg (0.225 mmol) of $P(o\text{-}Tol)_3$ was added rapidly to the reaction flask; wherein a molar ratio of $Pd_2(dba)_3$ and $P(o\text{-}Tol)_3$ was 1:15. After the reaction mixture was stirred under a stream of nitrogen for 15 minutes, the reaction mixture was heated to 60° C. for refluxing, and stirred for 60 hours then the reaction was stopped, after the reaction solution was cooled to room temperature, the reaction solution was dried to about 5 mL via reduced pressure distillation, then dropped into 300 mL of dry methanol, and continuously stirred for about 4 hours, a solid was gradually precipitated, a solid powder was obtained via suction filtration and dry. The solid powder was dissolved with chloroform, purified by neutral alumina column chromatography to remove the catalyst of $Pd_2(dba)_3$, the polymer solution was evaporated to about 5 mL, and the 5 mL solution was dropped into a methanol solvent and stirred for several hours, finally a polymer was collected and dried, the polymer was extracted with Soxhlet extractor, thus the monodispersity of the polymer molecular weight was improved.

GPC: $M_n$=56540, PDI=1.8.

Example 3

A benzodithiophene based copolymer containing thiophene pyrroledione units having a following structural formula is provided.

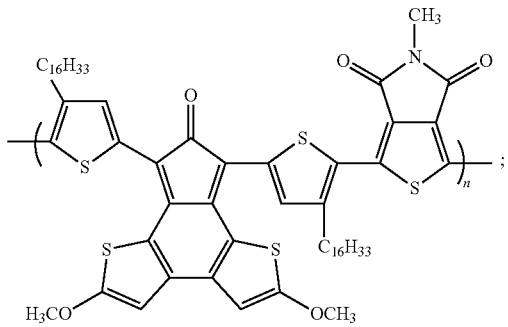

wherein $R_1$ is 16 alkyl, $R_2$ is H, $R_3$ is methoxyl; $R_4$ is H, $R_5$ is methyl, n=35.

Step one, the preparation of 2,5-dimethoxybenzene-7,9-bis(4-hexadecyl-5-trimethyltin-2-thiophene)-8H-cyclopentadiene benzo [1,2-b:4,3-b'] dithiophene-8-ketone was described below:

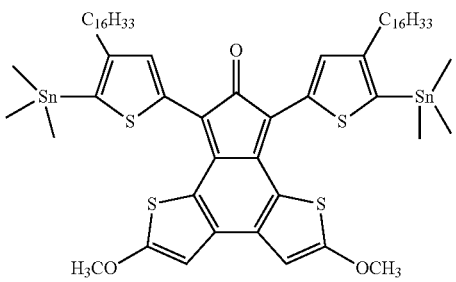

The synthesis method was referred to the steps one to four of Example 1.

MALDI-TOF-MS (m/z): 1241 (M⁺).

Step two, the preparation of benzodithiophene based copolymer containing thiophene pyrroledione units was described below:

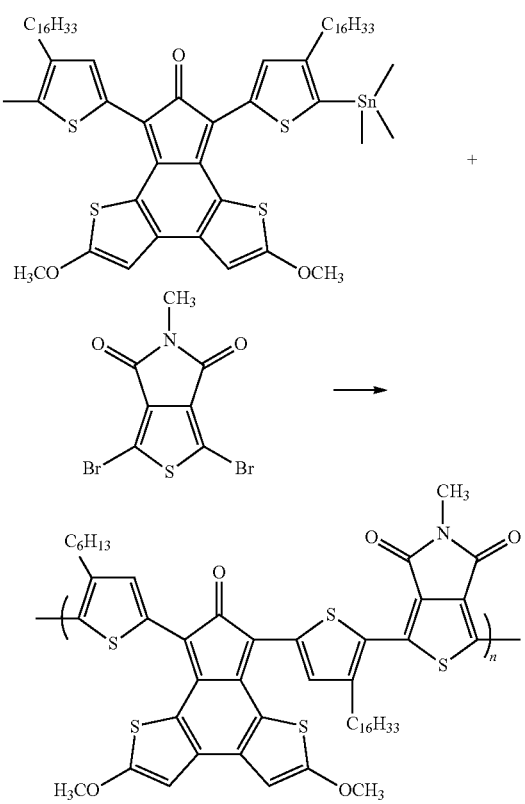

Under a nitrogen atmosphere, 0.74 g (0.6 mmol) of 2,5-dimethoxybenzene-7,9-bis(4-hexadecyl-5-trimethyltin-2-thiophene)-8H-cyclopentadiene benzo [1,2-b:4,3-b'] dithiophene-8-ketone and 0.16 g (0.5 mmol) of 1, 3-dibromo-5-methyl-4H-thiophene[3, 4-c] pyrrole-4, 5-dione were added to a reaction flask containing 10 mL of dry DMF, the reaction mixture was stirred under a stream of nitrogen for 15 minutes, and a catalyst of $Pd_2(dba)_3$ and $P(o\text{-}Tol)_3$ was added rapidly to the reaction flask; wherein the Pd$_2$(dba)$_3$ was 0.046 mg (0.00005 mmol, 0.01% mol), the P(o-Tol)$_3$ was 0.0304 mg (0.0001 mmol), a molar ratio of Pd$_2$(dba)$_3$ and P(o-Tol)$_3$ was 1:2. After the reaction mixture was stirred under a stream of nitrogen for 15 minutes, the reaction mixture was heated to 120° C. for refluxing, and stirred for 48 hours then the reaction was stopped, after the reaction solution was cooled to room temperature, the reaction solution was dried to about 5 mL via reduced pressure distillation, then dropped into 300 mL of dry methanol and continuously stirred for about 4 hours, a solid was gradually precipitated, a solid powder was obtained via suction filtration and dry. The solid powder was dissolved with chloroform, purified by neutral alumina column chromatography to remove the catalyst of Pd$_2$(dba)$_3$, the polymer solution was evaporated to about 5 mL, then the 5 mL solution was dropped into a methanol solvent and stirred for several hours, finally a polymer was collected and dried, the polymer was extracted with Soxhlet extractor, thus the monodispersity of the polymer molecular weight was improved.

GPC: Mn=37905, PDI=1.8.

Example 4

A benzodithiophene based copolymer containing thiophene pyrroledione units having a following structural formula is provided.

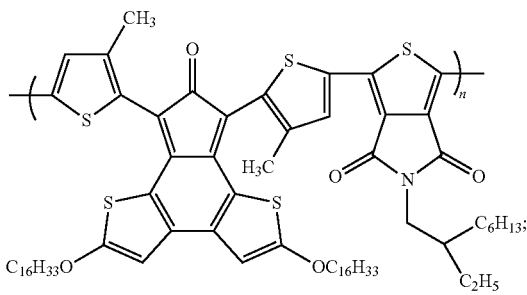

wherein R$_1$ is H, R$_2$ is methyl, R$_3$ is 16 alkoxy; R$_4$ is H, R$_5$ is 2-ethyl octyl, n=30.

Step one, the preparation of 2,5-di (hexadecyloxy)-7,9-bis (3-methyl-5-trimethyltin-2-thiophene)-8H-cyclopentadiene benzo [1,2-b:4,3-b'] dithiophene-8-ketone was described below:

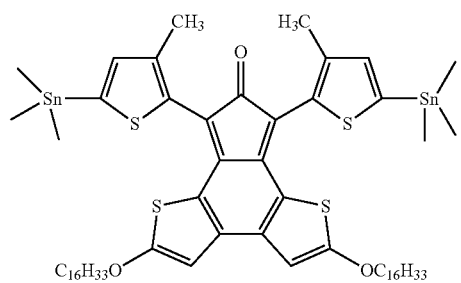

The synthesis method was referred to the steps one to four of Example 1.

MALDI-TOF-MS (m/z): 1241 (M$^+$).

Step two, the preparation of benzodithiophene based copolymer containing thiophene pyrroledione units was described below:

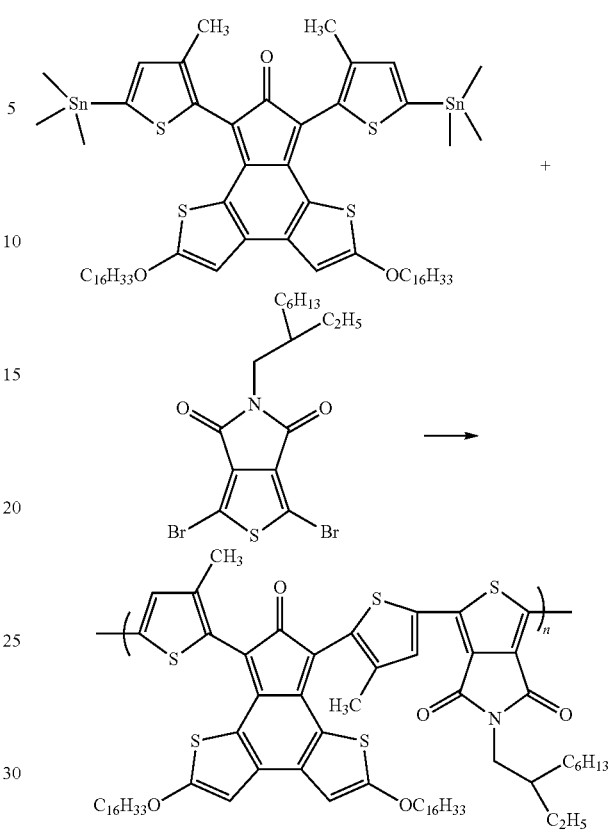

Under a nitrogen atmosphere, 0.62 g (0.5 mmol) of 2,5-di (hexadecyloxy)-7,9-bis(3-methyl-5-trimethyltin-2-thiophene)-8H-cyclopentadiene benzo [1,2-b:4,3-b'] dithiophene-8-ketone and 0.23 g (0.5 mmol) of 1, 3-dibromo-5-(2-ethyl octyl)-4H-thiophene [3, 4-c] pyrrole-4, 5-dione were added to a reaction flask containing 10 mL of dry DMF, the reaction mixture was stirred under a stream of nitrogen for 15 minutes, and a catalyst of 0.046 mg (0.00005 mmol, 0.01% mol) of Pd$_2$(dba)$_3$ and 0.0304 mg (0.0001 mmol) of P(o-Tol)$_3$ was added rapidly to the reaction flask; wherein a molar ratio of Pd$_2$(dba)$_3$ and P(o-Tol)$_3$ was 1:2. After the reaction mixture was stirred under a stream of nitrogen for 15 minutes, the reaction mixture was heated to 120° C. for refluxing, and stirred for 48 hours then the reaction was stopped, after the reaction solution was cooled to room temperature, the reaction solution was dried to about 5 mL via reduced pressure distillation, then dropped into 300 mL of dry methanol, and continuously stirred for about 4 hours, a solid was gradually precipitated, a solid powder was obtained via suction filtration and dry. The solid powder was dissolved with chloroform, purified by neutral alumina column chromatography to remove the catalyst of Pd$_2$(dba)$_3$, the polymer solution was evaporated to about 5 mL, then the 5 mL solution was dropped into a methanol solvent and stirred for several hours, finally a polymer was collected and dried, the polymer was extracted with Soxhlet extractor, thus the monodispersity of the polymer molecular weight was improved.

GPC: Mn=36150, PDI=1.8.

Example 5

A benzodithiophene based copolymer containing thiophene pyrroledione units having a following structural formula is provided.

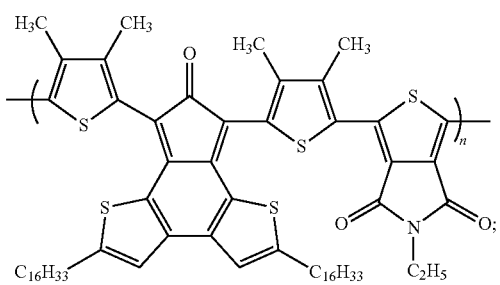

wherein $R_1$ and $R_2$ are identical methyl, $R_3$ is 16 alkoxy; $R_4$ is H, $R_5$ is ethyl, n=20.

Step one, the preparation of 2,5-di (hexadecyl)-7,9-bis(3, 4-dimethyl-5-trimethyltin-2-thiophene)-8H-cyclopentadiene benzo [1,2-b:4,3-b'] dithiophene-8-ketone was described below:

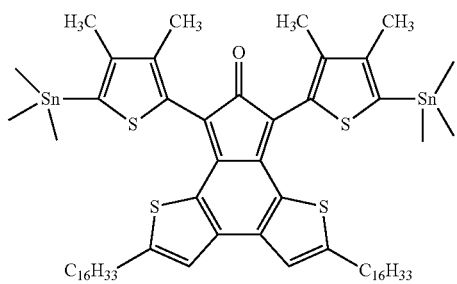

The synthesis method was referred to the steps one to four of Example 1.

MALDI-TOF-MS (m/z): 1237 (M$^+$).

Step two, the preparation of benzodithiophene based copolymer containing thiophene pyrroledione units was described below:

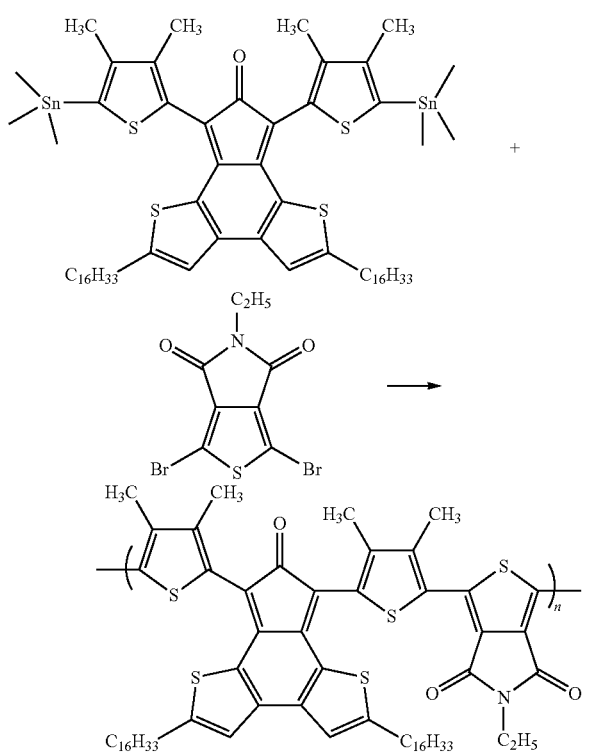

Under a nitrogen atmosphere, 0.62 g (0.5 mmol) of 2,5-di (hexadecyloxy)-7,9-bis(3, 4-dimethyl-5-trimethyltin-2-thiophene)-8H-cyclopentadiene benzo [1,2-b:4,3-b'] dithiophene-8-ketone and 0.17 g (0.5 mmol) of 1, 3-dibromo-5-ethyl-4H-thiophene [3, 4-c] pyrrole-4, 5-dione were added to a reaction flask containing 10 mL of dry benzene, the reaction mixture was stirred under a stream of nitrogen for 15 minutes, and a catalyst of 28.9 mg (0.025 mmol, 0.5% mol) of tetrakis(triphenylphosphine)palladium was added rapidly to the reaction flask. After the reaction mixture was stirred under a stream of nitrogen for 15 minutes, the reaction mixture was heated to 80° C. for refluxing, and stirred for 24 hours then the reaction was stopped, after the reaction solution was cooled to room temperature, the reaction solution was dried to about 5 mL via reduced pressure distillation, then dropped into 300 mL of dry methanol, and continuously stirred for about 4 hours, a solid was gradually precipitated, a solid powder was obtained via suction filtration and dry. The solid powder was dissolved with chloroform, purified by neutral alumina column chromatography to remove the catalyst of tetrakis(triphenylphosphine)palladium, the polymer solution was evaporated to about 5 mL, and the 5 mL solution was dropped into a methanol solvent and stirred for several hours, finally a polymer was collected and dried, the polymer was extracted with Soxhlet extractor, thus the monodispersity of the polymer molecular weight was improved.

GPC: Mn=21780, PDI=2.2.

Example 6

A benzodithiophene based copolymer containing thiophene pyrroledione units having a following structural formula is provided.

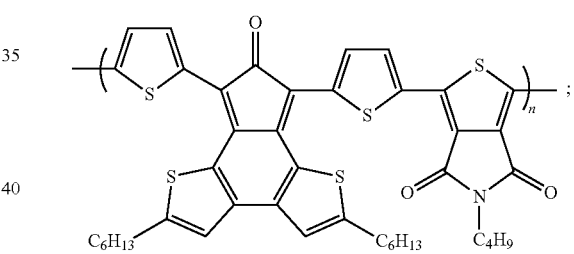

wherein $R_1$ and $R_2$ are identical H, $R_3$ is hexyl; $R_4$ is H, $R_5$ is butyl, n=15.

Step one, the preparation of 2,5-dihexyl-7,9-bis(5-trimethyltin-2-thiophene)-8H-cyclopentadiene benzo [1,2-b:4,3-b'] dithiophene-8-ketone was described below:

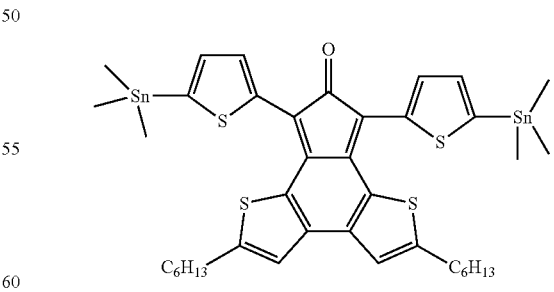

The synthesis method was referred to the steps one to four of Example 1.

MALDI-TOF-MS (m/z): 900 (M$^+$).

Step two, the preparation of benzodithiophene based copolymer containing thiophene pyrroledione units was described below:

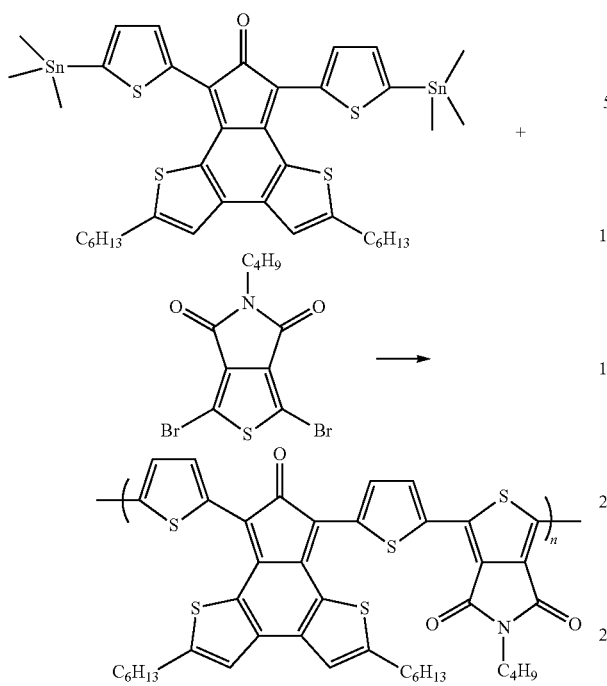

Under a nitrogen atmosphere, 0.45 g (0.5 mmol) of 2,5-dihexyl-7,9-bis(5-trimethyltin-2-thiophene)-8H-cyclopentadiene benzo [1,2-b:4,3-b'] dithiophene-8-ketone and 0.18 g (0.5 mmol) of 1, 3-dibromo-5-butyl-4H-thiophene [3, 4-c] pyrrole-4,5-dione were added to a reaction flask containing 10 mL of dry methylbenzene, the reaction mixture was stirred under a stream of nitrogen for 15 minutes, and a catalyst of 3.5 mg (0.005 mmol, 1% mol) of Pd(PPh$_3$)$_2$Cl$_2$ was added rapidly to the reaction flask. After the reaction mixture was stirred under a stream of nitrogen for 15 minutes, the reaction mixture was heated to 110° C. for refluxing, and stirred for 24 hours then the reaction was stopped, after the reaction solution was cooled to room temperature, the reaction solution was dried to about 5 mL via reduced pressure distillation, then dropped into 300 mL of dry methanol, and continuously stirred for about 4 hours, a solid was gradually precipitated, a solid powder was obtained via suction filtration and dry. The solid powder was dissolved with chloroform, purified by neutral alumina column chromatography to remove the catalyst of Pd(PPh$_3$)$_2$Cl$_2$, the polymer solution was evaporated to about 5 mL, and the 5 mL solution was dropped into a methanol solvent and stirred for several hours, finally a polymer was collected and dried, the polymer was extracted with Soxhlet extractor, thus the monodispersity of the polymer molecular weight was improved.

GPC: Mn=11700, PDI=2.2.

Example 7

A benzodithiophene based copolymer containing thiophene pyrroledione units having a following structural formula is provided.

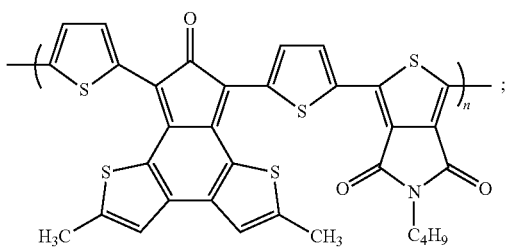

wherein R$_1$ and R$_2$ are identical H, R$_3$ is methyl; R$_4$ is H, R$_5$ is butyl, n=10.

Step one, the preparation of 2,5-dimethyl-7,9-bis(5-trimethyltin-2-thiophene)-8H-cyclopentadiene benzo [1,2-b:4,3-b'] dithiophene-8 ketone was described below:

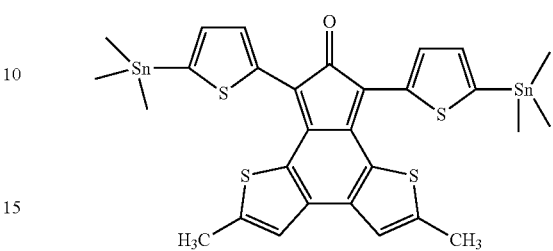

The synthesis method was referred to the steps one to four of Example 1.

MALDI-TOF-MS (m/z): 760 (M$^+$).

Step two, the preparation of benzodithiophene based copolymer containing thiophene pyrroledione units was described below:

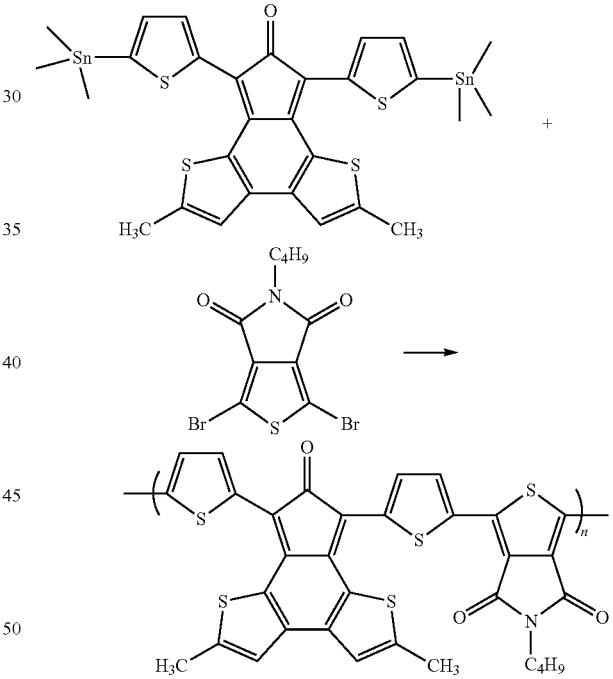

Under a nitrogen atmosphere, 0.38 g (0.5 mmol) of 2,5-dimethyl-7,9-bis(5-trimethyltin-2-thiophene)-8H-cyclopentadiene benzo [1,2-b:4,3-b'] dithiophene-8-ketone and 0.18 g (0.5 mmol) of 1, 3-dibromo-5-butyl-4H-thiophene [3, 4-c] pyrrole-4,5-dione were added to a reaction flask containing 10 mL of dry methylbenzene, the reaction mixture was stirred under a stream of nitrogen for 15 minutes, and a catalyst of 11.6 mg (0.01 mmol, 2% mol) of tetrakis(triphenylphosphine)palladium was added rapidly to the reaction flask. After the reaction mixture was stirred under a stream of nitrogen for 15 minutes, the reaction mixture was heated to 110° C. for refluxing, and stirred for 24 hours then the reaction was stopped, after the reaction solution was cooled to room temperature, the reaction solution was dried to about 5 mL via reduced pressure distillation, then dropped into 300 mL of dry methanol, and continuously stirred for about 4 hours, a solid was gradually precipitated, a solid powder was obtained via suction filtration and dry. The solid powder was dissolved with chloroform, purified by neutral alumina column chromatography to remove the catalyst of tetrakis(triphenylphosphine)palladium, the polymer solution was evaporated to about 5 mL, and the 5 mL solution was dropped into a methanol solvent and stirred for several hours, finally a polymer was collected and dried, the polymer was extracted with Soxhlet extractor, thus the monodispersity of the polymer molecular weight was improved.

GPC: Mn=12680, PDI=2.2.

Example 8

A benzodithiophene based copolymer containing thiophene pyrroledione units having a following structural formula is provided.

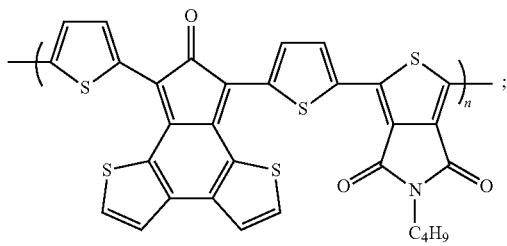

wherein $R_1$ and $R_2$ are identical H, $R_3$ and $R_4$ are identical H, $R_5$ is butyl, n=8.

Step one, the preparation of 7,9-bis(5-trimethyltin-2-thiophene)-8H-cyclopentadiene benzo [1,2-b:4,3-b'] dithiophene-8-ketone was described below:

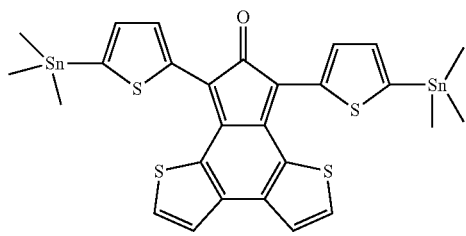

The synthesis method was referred to the steps one to four of Example 1.

MALDI-TOF-MS (m/z): 732 (M$^+$).

Step two, the preparation of benzodithiophene based copolymer containing thiophene pyrroledione units was described below:

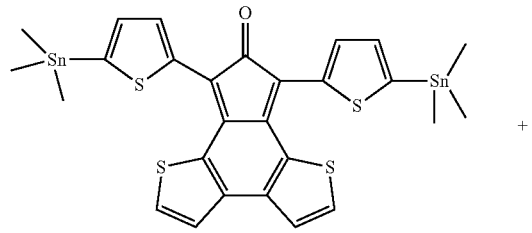

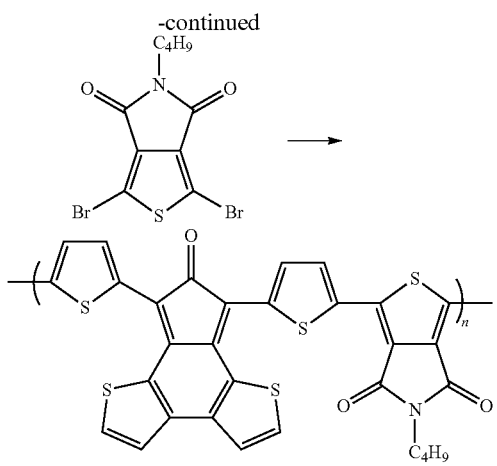

Under a nitrogen atmosphere, 0.37 g (0.5 mmol) of 7,9-bis (5-trimethyltin-2-thiophene)-8H-cyclopentadiene benzo [1,2-b:4,3-b'] dithiophene-8-ketone and 0.18 g (0.5 mmol) of 1, 3-dibromo-5-butyl-4H-thiophene[3, 4-c] pyrrole-4, 5-dione were added to a reaction flask containing 10 mL of dry benzene, the reaction mixture was stirred under a stream of nitrogen for 15 minutes, and a catalyst of 0.29 mg (0.00025 mmol, 0.05% mol) of tetrakis(triphenylphosphine)palladium was added rapidly to the reaction flask. After the reaction mixture was stirred under a stream of nitrogen for 15 minutes, the reaction mixture was heated to 80° C. for refluxing, and stirred for 12 hours then the reaction was stopped, after the reaction solution was cooled to room temperature, the reaction solution was dried to about 5 mL via reduced pressure distillation, then dropped into 300 mL of dry methanol, and continuously stirred for about 4 hours, a solid was gradually precipitated, a solid powder was obtained via suction filtration and dry. The solid powder was dissolved with chloroform, purified by neutral alumina column chromatography to remove the catalyst of tetrakis(triphenylphosphine)palladium, the polymer solution was evaporated to about 5 mL, and the 5 mL solution was dropped into a methanol solvent and stirred for several hours, finally a polymer was collected and dried, the polymer was extracted with Soxhlet extractor, thus the monodispersity of the polymer molecular weight was improved.

GPC: Mn=4896, PDI=2.3.

The present invention also provides use of benzodithiophene based copolymer containing thiophene pyrroledione units according to any of the above embodiment in polymer solar cell, polymer organic electroluminescent devices, polymer organic field effect transistors, polymer organic optical storage, polymer organic non-linear materials, or polymer organic laser. Several specific examples are given as follow.

Example 9

An organic solar cell device is provided using the copolymer of Example 1, i.e. the benzodithiophene based copolymer containing thiophene pyrroledione units is used as active layer material; the structure of the organic solar cell device is shown in FIG. 1.

Preparation of the organic solar cell device: the structure of the device was: glass/ITO/PEDOT:PSS/active layer/Al, wherein the ITO (indium tin oxide) was the indium tin oxide with a sheet resistance of 10 to 20Ω/sq, PEDOT was poly (3,4-ethylenedioxythiophene), PSS was poly(styrene sulfonic acid); ITO glass was cleaned by ultrasonic, treated with an oxygen-Plasma, and then the ITO glass was spin-coated with PEDOT:PSS. The copolymer of Example 1 was used as electron donor material and PCBM was used as the electron acceptor material, which was coated by spin-coating, the metal aluminum electrode was prepared by vacuum deposition techniques, the organic solar cell device was thus obtained.

Example 10

Figure 2:
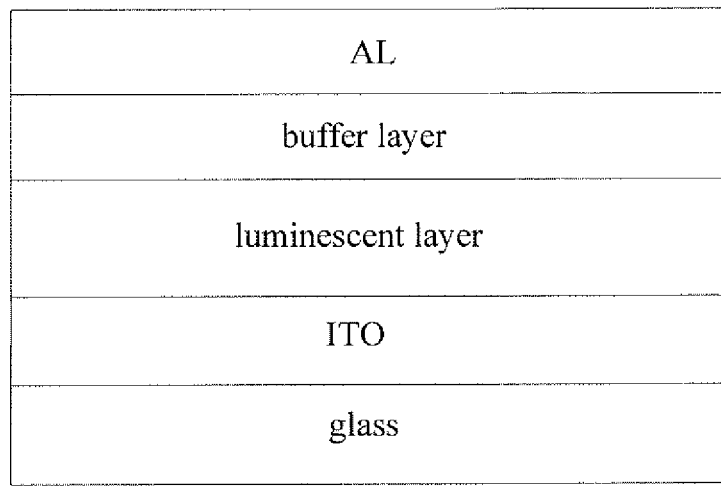
FIG. 2 is a schematic structure view of the organic electroluminescent device according to example 10.

An organic electroluminescent device is provided using the copolymer of Example 2, i.e. the benzodithiophene based copolymer containing thiophene pyrroledione units is used as active layer material; the structure of the organic electroluminescent device is shown in FIG. 2.

Preparation of the organic electroluminescent device: the structure of the device was: ITO/copolymer of the present invention/LiF/Al, an indium tin oxide (ITO) with a sheet resistance of 10 to 20Ω/sq was deposited on a glass to form a transparent anode, a layer of the copolymer of Example 2 was prepared on the ITO by spin-coating to form a luminescent layer, LiF was deposited on the luminescent layer by evaporation to form a buffer layer, finally, the metal Al was deposited on the buffer layer by vacuum evaporation to form the cathode of the device.

Example 11

Figure 3:
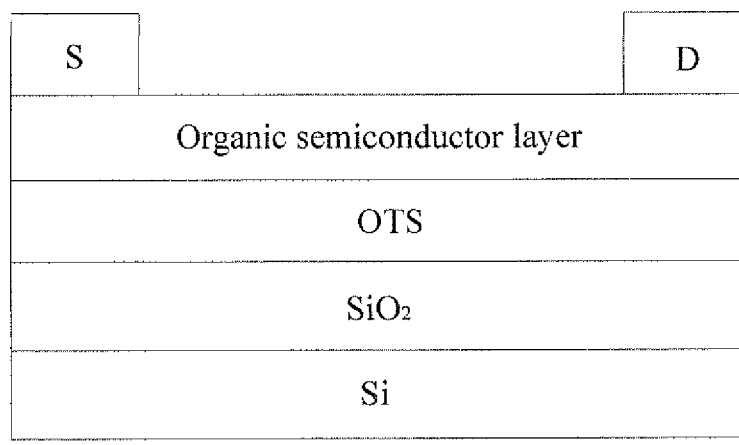
FIG. 3 is a schematic structure view of the organic field effect transistor according to example 11.

An organic field effect transistor is provided using the copolymer of Example 3, i.e. the benzodithiophene based copolymer containing thiophene pyrroledione units is used as organic semiconductor material; the structure of the organic field effect transistor is shown in FIG. 3.

Preparation of the organic field effect transistors: a heavily doped silicon (Si) wafer was used as substrate, an $SiO_2$ layer with a thick of 450 nm was used as an insulating layer, a source electrode (S) and a drain electrode (D) were made of gold, the copolymers of Example 3 was an organic semiconductor layer, which was spin-coated onto the $SiO_2$ layer modified with octadecyltrichlorosilane (OTS).

Applicant believes that, according to this description, those skilled in the art are sufficient to understand how to implement the invention, and assess the context defined by the claims may be implemented with the effect; those skilled in the art can determine and prove the benzodithiophene based copolymer containing thiophene pyrroledione units may be applied in the uses.

It should be understood that the preferred specific embodiments are specific and detailed, and should not be interpreted as limitations to the scope of the invention, as defined by the appended claims.

What is claimed is:

1. A benzodithiophene based copolymer containing thiophene pyrroledione units, having a structural formula:

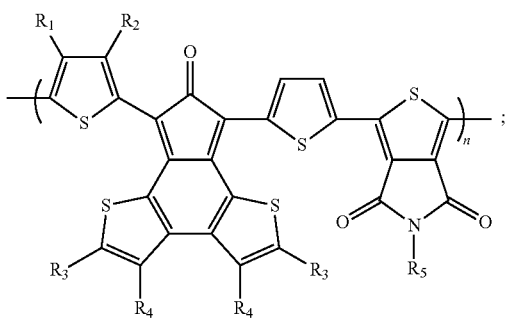

wherein $R_1$ and $R_2$ are selected from the group consisting of H, and $C_1$ to $C_{16}$ alkyl, respectively;

$R_3$ and $R_4$ are selected from the group consisting of H, $C_1$ to $C_{16}$ alkyl, $C_1$ to $C_{16}$ alkoxy, and thienyl substituted by $C_1$ to $C_{16}$ alkyl, respectively;

$R_5$ is $C_1$ to $C_{16}$ alkyl;

n is a natural number from 8 to 82.

2. The benzodithiophene based copolymer according to claim 1, wherein the alkyl is a linear alkyl or branched alkyl; the alkoxy is a linear alkoxy or branched alkoxy.

3. The benzodithiophene based copolymer according to claim 2, wherein n is a natural number from 9 to 60.

4. The benzodithiophene based copolymer according to claim 3, wherein $R_1$ is the same as $R_2$, and/or $R_3$ is the same as $R_4$.

5. The benzodithiophene based copolymer according to claim 3, wherein $R_1$, $R_2$, $R_3$, $R_4$ and $R_5$ are selected from a combination of:

$R_1$ and $R_2$ are H, $R_3$ and $R_4$ are methyl, $R_5$ is n-butyl; or $R_1$, $R_2$, $R_3$, and $R_4$ are H, $R_5$ is methyl; or $R_1$ is ethyl, $R_2$ is pentyl, $R_3$ is H, $R_4$ is 3-methyl thienyl, $R_5$ is 2-methyl butyl; or $R_1$ and $R_2$ are identical propyl, $R_3$ is 12 alkyl, $R_4$ is ethoxyl, $R_5$ is 2,4-dimethyl-3-ethyl heptyl; or $R_1$ is butyl, $R_2$ is 12 alkyl, $R_3$ is 14 alkoxy, $R_4$ is octyl, $R_5$ is 2,2,4-trimethyl pentyl; or $R_1$ and $R_2$ are identical H, $R_3$ is octoxy, $R_4$ is H, $R_5$ is 16alkyl; or $R_1$ is hexyl, $R_2$ is H, $R_3$ is 2-methyl thienyl, $R_4$ is H, $R_5$ is octyl: or $R_1$ is 16 alkyl, $R_2$ is H, $R_3$ is methoxyl, $R_4$ is H, $R_5$ is methyl; or $R_1$ is H, $R_2$ is methyl, $R_3$ is 16 alkoxy, $R_4$ is H, $R_5$ is butyl; or $R_1$ and $R_2$ are identical methyl, $R_3$ is 16 alkoxy, $R_4$ is H, $R_5$ is butyl; or $R_1$ and $R_2$ are identical H, $R_3$ is hexyl, $R_4$ is H, $R_5$ is butyl; or $R_1$ and $R_2$ are identical H, $R_3$ is methyl, $R_4$ is H, $R_5$ is butyl; or $R_1$ and $R_2$ are identical H, $R_3$ and $R_4$ are identical H, $R_5$ is butyl.

6. A method for preparing a benzodithiophene based copolymer containing thiophene pyrroledione units, comprising the steps of adding M1 and M2 to a solvent in an oxygen-free environment;

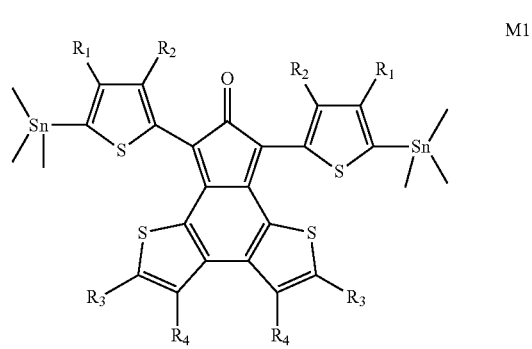

-continued

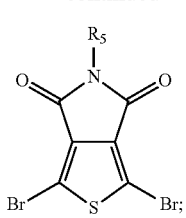
M2 performing a refluxing reaction in the presence of catalyst; the reaction formula is as follows:

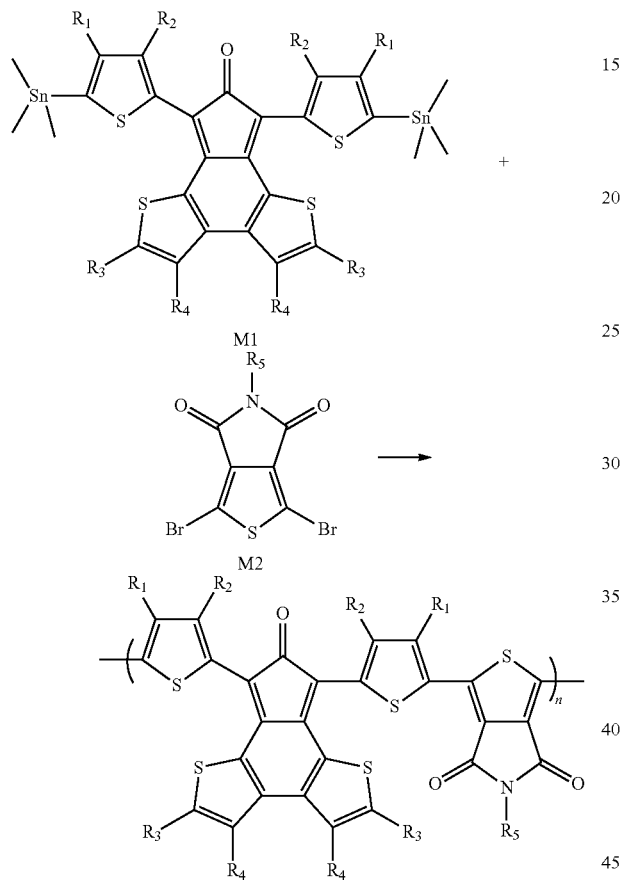

wherein $R_1$ and $R_2$ are selected from the group consisting of H, and $C_1$ to $C_{16}$ alkyl, respectively;
$R_3$ and $R_4$ are selected from the group consisting of H, $C_1$ to $C_{16}$ alkyl, $C_1$ to $C_{16}$ alkoxy, and thienyl substituted by $C_1$ to $C_{16}$ alkyl, respectively;
$R_5$ is $C_1$ to $C_{16}$ alkyl;
n is a natural number from 8 to 82;
a molar ratio between M1 and M2 is 1:1 to 1,5:1;
the solvent is at least one selected from the group consisting of toluene, tetrahydrofuran, benzene, and N,N-dimethylformamide;
the catalyst is organic palladium or a mixture of organic palladium and organic phosphine ligand, a molar amount of the catalyst is 0.01% to 5% of the molar amount of the M2;
the organic palladium is $Pd_2(dba)_3$, $Pd(PPh_3)_4$ or $Pd(PPh_3)_2Cl_2$, a molar ratio between the organic palladium and the organic phosphine ligand in the mixture is 1:2 to 1:20; the organic phosphine ligand is $P(o\text{-}Tol)_3$ or tricyclohexylphosphine;
the reaction is performed at a temperature ranging from 60° C. to 120° C. for 12 to 72 hours.

7. The method according to claim 6, wherein M1 is synthesized by the steps of:
S1, dissaving a compound A with a proper amount of dichloromethane to form a solution, under a nitrogen atmosphere, adding the solution dropwise to anhydrous dichloromethane containing 1,3-dicyclohexylcarbodiimide and 4-dimethylaminopyridine by a syringe; a molar ratio of the compound A, the 1,3-dicyciohexylcarbodiimide, and the 4-dimethylaminopyridine is 3:3:1, the reaction is performed for 8 to 24 hours to obtain a compound B, the reaction formula is as follows:

S2, adding the compound B and the compound C to a solvent according a molar ratio of 1:1, the solvent is ethanol or propanol;
heating to 78° C. to 100° C. to perform a refluxing reaction, then adding a reducing agent,
wherein the reducing agent is potassium hydroxide or sodium hydroxide, a molar ratio between the reducing agent and the compound B is 5:1; and reacting for additional 10 minutes after the reaction solution becomes dark green to obtain a compound D, S3, under a nitrogen atmosphere, dissolving the compound D to anhydrous tetrahydrofuran and cooling to −78° C.;
adding an n-hexane solution containing n-butyllithium slowly, wherein a molar ratio between the n-butyllithium and the compound is 1:2.5;
reacting under stirring at a temperature of −78°C for 2 hours;
then adding trimethyl tin chloride, wherein a molar ratio between the trimethyl tin chloride and the compound D is 2.5:1;
incubating for 0.5 hours and then returning to room temperature; and reacting for additional 24 hours to obtain the compound Mi; the reaction formula is as follows:

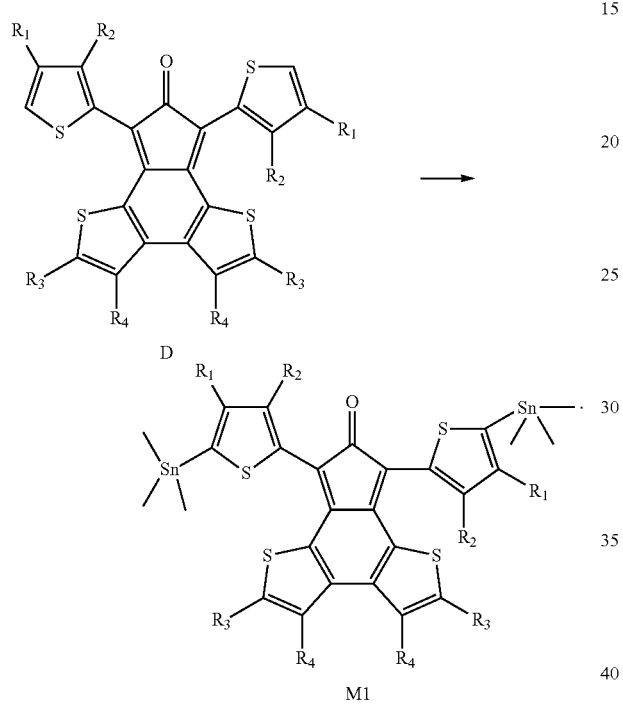

8. The method according to claim 7, wherein the alkyl is a linear alkyl or branched alkyl; the alkoxy is a linear alkoxy or branched alkoxy, and n is a natural number from 9 to 60.

9. The method according to claim 8, wherein $R_1$ is the same as $R_2$, and/or $R_3$ is the same as $R_4$; or $R_1$, $R_2$, $R_3$, $R_4$ and $R_5$ are selected from a combination of:

$R_1$ and $R_2$ are H, $R_3$ and $R_4$ are methyl, $R_5$ is n-butyl; or $R_1$, $R_2$, $R_3$, and $R_4$ are H, $R_5$ is methyl; or $R_1$ is ethyl, $R_2$ is pentyl, $R_3$ is H, $R_4$ is 3-methyl thienyl, $R_5$ is 2-methyl butyl; or $R_1$ and $R_2$ are identical propyl, $R_3$ is 12 alkyl, $R_4$ is ethoxyl, $R_5$ is 2,4-dimethyl-3-ethyl heptyl; or $R_1$ is butyl, $R_2$ is 12 alkyl, $R_3$ is 14 alkoxy, $R_4$ is octyl, $R_5$ is 2,2,4-trimethyl pentyl; or $R_1$ and $R_2$ are identical H, $R_3$ is octoxy, $R_4$ is H, $R_5$ is 16 alkyl; or $R_1$ is hexyl, $R_2$ is H, $R_3$ is 2-methyl thienyl, $R_4$ is H, $R_5$ is octyl, or $R_1$ is 16 alkyl, $R_2$ is H, $R_3$ is methoxyl, $R_4$ is H, $R_5$ is methyl; or $R_1$ is H, $R_2$ is methyl, $R_3$ is 16 alkoxy, $R_4$ is H, $R_5$ is butyl; or $R_1$ and $R_2$ are identical methyl, $R_3$ is 16 alkoxy, $R_4$ is H, $R_5$ is butyl; or $R_1$ and $R_2$ are identical H, $R_3$ is hexyl, $R_4$ is H, $R_5$ is butyl; or $R_1$ and $R_2$ are identical H, $R_3$ is methyl, $R_4$ is H, $R_5$ is butyl; or $R_1$ and $R_2$ are identical H, $R_3$ and $R_4$ are identical H, $R_5$ is butyl.

10. benzodithiophene based copolymer containing thiophene pyrroledione units according to claim 1 polymer solar cells, polymer organic electroluminescent devices, polymer organic field effect transistors, polymer organic optical storage, polymer organic non-linear devices, or polymer organic laser.

* * * * *